United States Patent
Dipierro

(10) Patent No.: US 11,920,156 B2
(45) Date of Patent: Mar. 5, 2024

(54) ENGINEERED NATURAL KILLER (NK) CELLS AND COMPOSITIONS AND METHODS THEREOF

(71) Applicant: Indapta Therapeutics, Inc., Seattle, WA (US)

(72) Inventor: Guy Dipierro, Seattle, WA (US)

(73) Assignee: Indapta Therapeutics, Inc., Houston, TX (US)

( * ) Notice: Subject to any disclaimer, the term of this patent is extended or adjusted under 35 U.S.C. 154(b) by 630 days.

(21) Appl. No.: 16/484,813

(22) PCT Filed: Feb. 8, 2018

(86) PCT No.: PCT/US2018/017493
§ 371 (c)(1),
(2) Date: Aug. 8, 2019

(87) PCT Pub. No.: WO2018/148462
PCT Pub. Date: Aug. 16, 2018

(65) Prior Publication Data
US 2019/0376036 A1    Dec. 12, 2019

Related U.S. Application Data

(60) Provisional application No. 62/484,350, filed on Apr. 11, 2017, provisional application No. 62/457,098, filed on Feb. 9, 2017.

(51) Int. Cl.
*C12N 5/0783* (2010.01)
*A61K 35/17* (2015.01)
*A61P 35/00* (2006.01)
*C07K 14/725* (2006.01)
*C07K 14/735* (2006.01)
*C07K 16/28* (2006.01)
*C12N 9/22* (2006.01)
*C12N 15/11* (2006.01)
*C12N 15/113* (2010.01)

(52) U.S. Cl.
CPC ............ *C12N 5/0646* (2013.01); *A61K 35/17* (2013.01); *A61P 35/00* (2018.01); *C07K 14/7051* (2013.01); *C07K 14/70535* (2013.01); *C07K 16/2887* (2013.01); *C12N 9/22* (2013.01); *C12N 15/11* (2013.01); *C12N 15/1138* (2013.01); *C07K 2317/24* (2013.01); *C07K 2317/732* (2013.01); *C07K 2317/76* (2013.01); *C07K 2319/30* (2013.01); *C12N 2310/14* (2013.01); *C12N 2310/20* (2017.05); *C12N 2510/00* (2013.01); *C12N 2800/80* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,889,818 A | 12/1989 | Gelfand et al. |
| 5,350,674 A | 9/1994 | Boenisch et al. |
| 5,585,362 A | 12/1996 | Wilson et al. |
| 5,641,870 A | 6/1997 | Rinderknecht et al. |
| 5,716,613 A | 2/1998 | Guber et al. |
| 5,716,826 A | 2/1998 | Gruber et al. |
| 5,851,529 A | 12/1998 | Guber et al. |
| 6,168,991 B1 | 1/2001 | Choi et al. |
| 6,428,968 B1 | 8/2002 | Molnar-Kimber et al. |
| 6,506,559 B1 | 1/2003 | Fire et al. |
| 6,632,670 B1 | 10/2003 | Wadsworth et al. |
| 6,635,472 B1 | 10/2003 | Lauermann |
| 6,653,103 B2 | 11/2003 | Petersen et al. |
| 6,689,871 B1 | 2/2004 | Wolfe et al. |
| 6,723,316 B2 | 4/2004 | Laquerre et al. |
| 6,897,045 B2 | 5/2005 | Engelhardt et al. |
| 7,001,765 B2 | 2/2006 | Maass et al. |
| 7,033,826 B2 | 4/2006 | Perricaudet et al. |
| 7,153,510 B1 | 12/2006 | Rose |
| 7,172,893 B2 | 2/2007 | Rabinowitz et al. |
| 7,238,526 B2 | 7/2007 | Wilson et al. |
| 7,241,447 B1 | 7/2007 | Engelhardt et al. |
| 7,537,924 B2 | 5/2009 | Coffin |
| 7,550,296 B2 | 6/2009 | Hermiston et al. |
| 7,588,767 B2 | 9/2009 | Szalay et al. |
| 7,588,771 B2 | 9/2009 | Szalay et al. |
| 7,662,627 B2 | 2/2010 | Johnson et al. |
| 7,731,952 B2 | 6/2010 | Mohr et al. |
| 7,731,974 B2 | 6/2010 | Bell et al. |
| 7,754,221 B2 | 7/2010 | Szalay et al. |
| 7,811,814 B2 | 10/2010 | Bohn et al. |
| 7,662,398 B2 | 12/2010 | Szalay et al. |
| 7,897,146 B2 | 3/2011 | Brown et al. |
| 7,906,111 B2 | 3/2011 | Wilson et al. |
| 7,927,585 B2 | 4/2011 | Snyder |

(Continued)

FOREIGN PATENT DOCUMENTS

| | | |
|---|---|---|
| EP | 1520175 B1 | 11/2007 |
| EP | 1606411 B1 | 12/2008 |

(Continued)

OTHER PUBLICATIONS

Binyamin, Liat et al. Journal of immunology (Baltimore, Md.: 1950) vol. 180,9 (2008): 6392-401. doi:10.4049/jimmunol.180.9. 6392 (Year: 2008).*

(Continued)

*Primary Examiner* — Michael Szperka
*Assistant Examiner* — Lia E Taylor
(74) *Attorney, Agent, or Firm* — Morrison & Foerster LLP

(57) ABSTRACT

The present invention provides engineered Natural Killer (NK) cells and methods of producing engineered NK cells. The engineered NK cells and compositions containing the engineered NK cells are useful for treating diseases such as cancer.

18 Claims, 1 Drawing Sheet

Specification includes a Sequence Listing.

(56) References Cited

U.S. PATENT DOCUMENTS

| | | | |
|---|---|---|---|
| 7,943,374 B2 | 5/2011 | Hildinger | |
| 7,968,340 B2 | 6/2011 | Hallek et al. | |
| 8,007,780 B2 | 8/2011 | Arbetman | |
| 10,066,207 B2 | 9/2018 | Kim et al. | |
| 2004/0009604 A1 | 1/2004 | Zhang et al. | |
| 2004/0063094 A1 | 4/2004 | Coffin et al. | |
| 2005/0220818 A1 | 10/2005 | Lorence | |
| 2005/0260601 A1 | 11/2005 | Whitt | |
| 2006/0039894 A1 | 2/2006 | Mohr et al. | |
| 2006/0292156 A1* | 12/2006 | Campbell | A61K 35/17 424/155.1 |
| 2007/0098743 A1 | 5/2007 | Bell et al. | |
| 2007/0110720 A1 | 5/2007 | Brown et al. | |
| 2007/0202572 A1 | 8/2007 | Szalay et al. | |
| 2007/0212727 A1 | 9/2007 | Szalay et al. | |
| 2008/0247990 A1 | 10/2008 | Campbell | |
| 2009/0010889 A1 | 1/2009 | Brown et al. | |
| 2009/0053244 A1 | 2/2009 | Chen et al. | |
| 2009/0098529 A1 | 4/2009 | Chen et al. | |
| 2009/0117034 A1 | 5/2009 | Chen et al. | |
| 2009/0136917 A1 | 5/2009 | Szalay et al. | |
| 2009/0155287 A1 | 6/2009 | Chen et al. | |
| 2009/0162288 A1 | 6/2009 | Chen et al. | |
| 2009/0215147 A1 | 8/2009 | Zhang et al. | |
| 2009/0274728 A1 | 11/2009 | Brown et al. | |
| 2009/0285860 A1 | 11/2009 | Martuza et al. | |
| 2010/0062016 A1 | 3/2010 | Szalay et al. | |
| 2010/0092515 A1 | 4/2010 | Conner et al. | |
| 2010/0113567 A1 | 5/2010 | Barber | |
| 2010/0172877 A1 | 7/2010 | Van Den Pol | |
| 2010/0178684 A1 | 7/2010 | Woo et al. | |
| 2010/0196325 A1 | 8/2010 | Szalay et al. | |
| 2010/0233078 A1 | 9/2010 | Szalay et al. | |
| 2011/0064650 A1 | 3/2011 | Szalay | |
| 2011/0158948 A1 | 6/2011 | Brown et al. | |
| 2011/0177032 A1 | 7/2011 | Martuza et al. | |
| 2011/0212530 A1 | 9/2011 | Baltimore et al. | |
| 2013/0295044 A1* | 11/2013 | Kim | C12N 5/0646 435/325 |
| 2014/0086890 A1 | 3/2014 | Childs et al. | |
| 2014/0154216 A1 | 6/2014 | Coffin | |
| 2016/0339066 A1 | 11/2016 | Szalay et al. | |
| 2017/0137784 A1 | 5/2017 | Masuyama | |
| 2019/0376036 A1 | 12/2019 | DiPierro | |

FOREIGN PATENT DOCUMENTS

| | | | |
|---|---|---|---|
| EP | 1385466 B1 | 3/2011 | |
| EP | 3539553 | 9/2019 | |
| JP | 2002504357 A | 2/2002 | |
| WO | WO 1999038955 A2 | 8/1999 | |
| WO | WO-1999043208 A1 | 9/1999 | |
| WO | WO-2005118854 A1 | 12/2005 | |
| WO | WO 2007052029 A1 | 5/2007 | |
| WO | WO-2010110734 A1 | 9/2010 | |
| WO | WO 2012061814 A1 | 5/2012 | |
| WO | WO-2009041113 A1 | 9/2013 | |
| WO | WO-2016011210 A2 * | 1/2016 | A61K 35/17 |
| WO | WO-2016077734 A2 * | 5/2016 | A61K 35/17 |
| WO | WO-2016201300 A1 | 12/2016 | |
| WO | WO-2017017184 A1 | 2/2017 | |
| WO | WO 2017/048809 | 3/2017 | |
| WO | WO 2017/078807 | 5/2017 | |
| WO | WO 2017/079673 | 5/2017 | |
| WO | WO 2017/127729 | 7/2017 | |
| WO | WO 2017127755 | 7/2017 | |
| WO | WO 2018/148462 | 8/2018 | |
| WO | WO 2019/222293 | 11/2019 | |
| WO | WO 2020/107002 | 5/2020 | |

OTHER PUBLICATIONS

Beurdeley et al., "Compact designer TALENs for efficient genome engineering," Nat Commun. (2013) 4:1762.

Beziat et al., "CMV drives clonal expansion of NKG2C1NK cellsexpressing self-specific KIRs in chronic hepatitis patients," Eur. J. Immunol. (2012) 42: 447-457.

Boerner et al., "Production of Antigen-Specific Human Monoclonal Antibodies From in Vitro-Primed Human Splenocytes," J Immunol (1991) 147 (1), 86-95 (Abstract only).

Bottino et al., "NK cell activating receptors and tumor recognition in humans," Curr Top Microbiol Immunol. (2006) 298: 175-82.

Bryceson et al., "Line of attack: NK cell specificity and integration of signals," Curr Opin Immunol. (2008) 20(3): 344-52.

Caligiuri et al., "Human natural killer cells," Blood. (2008) Aug. 1;112(3):461-469.

Chevalier et al., "Homing endonucleases: structural and functional insight into the catalysts of intron/intein mobility," Nucleic Acids Res. (2001) 29(18): 3757-74.

Childs et al., "Bringing Natural Killer Cells to the Clinic: Ex Vivo Manipulation," American Society of Hematology (2013) 2013:234-246.

Cichocki et al., "CD56dimCD57+NKG2C+ NK cell expansion is associated with reduced leukemia relapse after reduced intensity HCT," Leukemia. (2016) 30(2): 456-463.

Cichocki et al., "GSK 3 inhibition drives maturation of NK cells and enhances their antitumor activity," Cancer Res. (2017) 77(20): 5664-5675.

Cichocki et al., "The Past, Present, and Future of NK Cells in Hematopoietic Cell Transplantation and Adoptive Transfer," Curr Top Microbiol Immunol. (2016) 395: 225-243.

Costa-Garcia et al., "Antibody-Mediated Response of NKG2Cbright NK Cells against Human Cytomegalovirus," J Immunol (2015) 194(6): 2715-2724.

Dahlberg et al., "Natural Killer Cell-Based Therapies Targeting Cancer: Possible Strategies to Gain and Sustain Anti-Tumor Activity," Frontiers in Immunology, (2015) vol. 6 article 605; pp. 1-19.

Durai et al., "Zinc finger nucleases: custom-designed molecular scissors for genome engineering of plant and mammalian cells," Nucleic Acids Res. (2005) 33(18): 5978-90.

Fire et al., "Potent and specific genetic interference by double-stranded RNA in Caenorhabditis elegans," Nature (1998) 391: 806-811.

Fire, A., "RNA-triggered gene silencing," Trends Genet. (1999) 15(9): 358-63.

Foley et al., "Cytomegalovirus reactivation after allogeneic transplantation promotes a lasting increase in educated NKG2C+ natural killer cells with potent function," Blood. (2012) 119(11): 2665-2674.

Gong et al., "Characterization of a human cell line (NK-92) with phenotypical and functional characteristics of activated natural killer cells," Leukemia. (1994) 8(4):652-8.

Hoogenboom et al., "Multi-subunit proteins on the surface of filamentous phage: methodologies for displaying antibody (Fab) heavy and light chains," Nucleic Acids Res. (1991) 19(15):4133-4137.

Hwang et al., "Identification of human NK cells that are deficient for signaling adaptor FcRγ and specialized for antibody-dependent immune functions," Int Immunol. (2012) 24(12): 793-802.

Klingemann et al., "Natural Killer Cells for Immunotherapy - Advantages of the NK-92 Cell Line over Blood NK Cells," Frontiers in Immunology, (2016) vol. 7, article 91 pp. 1-7.

Klingemann, H., "P33. NK-92 cellular immunotherapy as an alternative to donor derived peripheral blood NK cells,", J Immunother Cancer (2014) 2(Suppl 2): P24.

Lanier, "Up on the tightrope: natural killer cell activation and inhibition," Nat Immunol. (2008) 9(5): 495-502.

Lee et al., "Epigenetic modification and antibody-dependent expansion of memory-like NK cells in human cytomegalovirus-infected individuals," Immunity. (2015) 42(3):431-42.

Lonberg et al., "Human antibodies from transgenic mice," Int Rev Immunol. (1995) 13(1): 65-93.

Lopez-Verges et al., "Expansion of a unique CD57+NKG2Chi natural killer cell subset during acute human cytomegalovirus infection," PNAS (2011) 108(36): 14725-14732.

Mak et al., "TAL effectors: function, structure, engineering and applications," Curr Opin Struct Biol. (2013) 23(1): 93-9.

(56) References Cited

OTHER PUBLICATIONS

Mali et al., "Cas9 as a versatile tool for engineering biology," Nat. Methods (2013) 10(10): 957-963.
Marks et al., "Molecular evolution of proteins on filamentous phage. Mimicking the strategy of the immune system," J Biol Chem. (1992) 267(23): 16007-10.
Mumtaz et al., "Design of liposomes for circumventing the reticuloendothelial cells," Glycobiology. (1991) 1(5):505-510.
Nagashima et al., "Stable transduction of the interleukin-2 gene into human natural killer cell lines and their phenotypic and functional characterization in vitro and in vivo," Blood. (1998) 91(10): 3850-3861.
Ran et al., "Genome engineering using the CRISPR-Cas9 system," Nat Protoc. (2013) 8(11): 2281-2308.
Roda et al., "Natural killer cells produce T cell-recruiting chemokines in response to antibody-coated tumor cells," Cancer Res. (2006) 66(1): 517-526.
Schlums et al., "Cytomegalovirus infection drives adaptive epigenetic diversification of NK cells with altered signaling and effector function," Immunity. (2015) 42(3): 443-456.
Stewart et al., "Strategies of natural killer cell recognition and signaling," Curr Top Microbiol Immunol. (2006) 298: 1-21.
Stoddard, "Homing endonuclease structure and function," Q Rev Biophys. (2005) 38(1): 49-95.
Vivier et al., "Innate or adaptive immunity? The example of natural killer cells," Science. (2011) 331(6013): 44-49.
Zapata et al., "Engineering Linear F(ab')2 Fragments For Efficient Production In *Escherichia coli* And Enhanced Antiproliferative Activity," Protein Engineering (1995) 8(10): 1057-1062.
Zhang et al., "Antibody-dependent memory-like NK cells distinguished by FcRγ-deficiency," J Immunol. (2013) 190(4): 1402-1406.
Bigley et al., "Latent cytomegalovirus infection enhances antitumour cytotoxicity through accumulation of NKG2C+ Nk cells in healthy humans," Clin Exp Immunol. (2016) 185(2): 239-51.
Bigley et al., "Cytomegalovirus: an unlikely ally in the fight against blood cancers?," Clin Exp Immunol. (2018) 193(3): 265-274.
Capuano et al., "Tumor-Targeting Anti-CD20 Antibodies Mediate In Vitro Expansion of Memory Natural Killer Cells: Impact of CD16 Affinity Ligation Conditions and In Vivo Priming," Front Immunol. (2018) 9:1031.
Dubois et al., "Preassociation of IL-15 with IL-15R alpha-IgG1-Fc enhances its activity on proliferation of NK and CD8+/CD44high T cells and its antitumor action," J Immunol. (2008) 180(4): 2099-106.
Zhang et al., "Cutting edge: antibody-dependent memory-like NK cells distinguished by FcRγ deficiency," J Immunol. 2013;190(4):1402-6.
Alici et al. "Autologous antitumor activity by NK cells expanded from myeloma patients using GMP-compliant components," Blood, (2008). 111(6):3155-62.
Alici et al. "Anti-myeloma activity of endogenous and adoptively transferred activated natural killer cells in experimental multiple myeloma model," Exp Hematol, (2007). 35(12):1839-1846.
Bachanova et al., "NK cells in therapy of cancer," Grit Rev Oncog, (2014). 19(1-2):133-141.
Balasa et al., "Elotuzumab enhances natural killer cell activation and myeloma cell killing through interleukin-2 and TNF-α pathways." Cancer Immunol Immunother, (2015). 64:61-73, 13 pages.
Benson et al., "IPH2101, a novel anti-inhibitory KIR antibody, and lenalidomide combine to enhance the natural killer cell versus multiple myeloma effect," Blood, (2011). 118(24):6387-6391.
Brunetta, et al., "Chronic HIV-1 viremia reverses NKG2A/NKG2C ratio on natural killer cells in patients with human cytomegalovirus co-infection," AIDS, (2010) 24(1):27-34.
Burns et al., "IL-2-based immunotherapy after autologous transplantation for lymphoma and breast cancer induces immune activation and cytokine release: a phase I/II trial," Bone Marrow Transplant, (2003). 32(2):177-86.

Castagna et al., "Re-discovering NK cell allo-reactivity in the; therapy of solid tumors," J Immunotherapy Cancer, (2016). 4:54, 3 pages.
Chan et al., "Antibody-dependent cell-mediated cytotoxicity overcomes NK cell-resistance in MLL-rearranged leukemia expressing inhibitory KIR ligands but not activating ligands," Clin Cancer Res, (2012). 18(22):6296-6305.
Chen et al., "Cetuximab intensifies the ADCC activity of adoptive NK cells in a nude mouse colorectal cancer xenograft model," Oncol Lett, (2016). 12(3):1868-1876.
Fujii et al. "A potential therapy for chordoma via antibody-dependent cell-mediated cytotoxicity (ADCC) employing NK or high affinity NK (haNK) cells in combination with cetuximab" J Neurosurg., (2018). 128(5):1419-1427.
Fujisaki et al., "Expansion of highly cytotoxic human natural killer cells for cancer cell therapy," Cancer Res, (2009). 69(9):4010-4017.
Lee et al., "Epigenetic Modification and Antibody-Dependent Expansion of Memory-like NK Cells in Human Cytomegalovirus-Infected Individuals," Immunity, (2015). 42:431-442, 20 pages.
Lee et al., "Formation of FcRγ -deficient NK cell subset associated with HCMV-reactivation in hematopoietic cell transplant recipients." Journal of Clinical Oncology, (2017). 35(7):131, 3 pages.
Lee et al., "HLA-E surface expression depends on binding of TAP-dependent peptides derived from certain HLA class I signal sequences," J Immunol., (1998). 160(10):4951-60.
Lin et al., "Handbook of Practical Immunohistochemistry, Table of Contents," 2nd Ed., Springer, 2015, 5 pages.
Liu et al., "FcR gamma Gene Editing Reprograms Conventional NK Cells to Display Key Features of Adaptive Human NK Cells," iScience, (2020). 23:101709, 10 pages.
Miltenyi Biotec Handbook (2022, pp. 1-7) (Year: 2022).
Parkhurst et al., "Adoptive transfer of autologous natural killer cells leads to high levels of circulating natural killer cells but does not mediate tumor regression," Clin Cancer Res., (2011). 17(19):6287-97.
Sutlu et al., "Clinical-grade, large-scale, feeder-free expansion of highly active human natural killer cells for adoptive immunotherapy using an automated bioreactor." Cytotherapy, (2010). 12(8):1044-55.
Takai T et al. "FcR gamma chain deletion results in pleiotrophic effector cell defects." Cell, (1994). 76(3):519-29, 12 pages.
Adams et al., "Ambiguous allele combinations in HLA Class I and Class II sequence-based typing: when precise nucleotide sequencing leads to imprecise allele identification," J Transl Med. (2004) 2(1): 30.
Allen et al., "Retargeted oncolytic measles strains entering via the EGFRγIII receptor maintain significant antitumor activity against gliomas with increased tumor specificity," Cancer Res. (2006) 66(24): 11840-50.
Amersdorfer et al., "Molecular characterization of murine humoral immune response to botulinum neurotoxin type A binding domain as assessed by using phage antibody libraries," Infect Immun. (1997) 65(9): 3743-52.
Anfossi et al., "Human NK Cell Education by Inhibitory Receptors for MHC Class I," Immunity, 25(2): 331-342 (2006).
Bae et al., "Extracellular matrix for a rechargeable cell delivery system," J Control Release. (1998) 53(1-3): 249-58.
Benecia et al., "HSV oncolytic therapy upregulates interferon-inducible chemokines and recruits immune effector cells in ovarian cancer," Mol Ther. (2005) 12(5): 789-802.
Bhat et al., "Enhancement of NK cell antitumor responses using an oncolytic parvovirus," Int J Cancer. (2011) 128(4): 908-19.
Bhat et al., "NK-cell-dependent killing of colon carcinoma cells is mediated by natural cytotoxicity receptors (NCRs) and stimulated by parvovirus infection of target cells," BMC Cancer. (2013) 13:367.
Bida et al., "2B4 utilizes ITAM-containing receptor complexes to initiate intracellular signaling and cytolvsis," Molecular immunology, 48(9-10): 1149-1159 (2011), 23 pages.
Bigley et al., "Acute exercise preferentially redeploys NK-cells with a highly-differentiated phenotype and augments cytotoxicity against lymphoma and multiple myeloma target cells," Brain Behav Immun. (2014) 39:160-71.

(56) References Cited

OTHER PUBLICATIONS

Bigley et al., "NK cell function is impaired during long-duration spaceflight," J Appl Physiol. (2018) 126:842-853.
Bjorkstrom et al., "Expression patterns of NKG2A, Kir, and CD57 define a process of CD56dim NK-cell differentiation uncoupled from NK-cell education," Blood, 116(19):3853-3864 (2010).
Bouhadir et al., "Degradation of partially oxidized alginate and its potential application for tissue engineering," Biotechnol Prog. (2001) 17(5): 945-50.
Brandt et al., "The B7 family member B7-H6 is a tumor cell ligand for the activating natural killer cell receptor NKp30 in humans," Journal of Experimental Medicine, 206(7): 1495-1503 (2009).
Bryant et al., "The effects of scaffold thickness on tissue engineered cartilage in photocrosslinked poly(ethylene oxide) hydrogels," Biomaterials. (2001) 22(6): 619-26.
Campbell et al., "Structure/function of human killer cell immunoglobulin-like receptors: lessons from polymorphisms, evolution, crystal structures and mutations," Immunology, 132(3): 315-325 (2011).
Carter et al., "Humanization of an anti-p185HER2 antibody for human cancer therapy," Proc Natl Acad Sci U S A. (1992) 89(10): 4285-9.
Carter, "Potent antibody therapeutics by design," Nature Reviews Immunology, 6(5): 343-357 (2006).
Cartron et al., "Therapeutic activity of humanized anti-CD20 monoclonal antibody and polymorphism in IgG Fc receptor FcγRIIIa gene," Blood. (2002) 99(3): 754-758.
Cha et al., "Human cytomegalovirus clinical isolates carry at least 19 genes not found in laboratory strains," Journal of Virology, 70: 78-83 (1996).
Chen et al., "Antibody mapping to domains of botulinum neurotoxin serotype A in the complexed and uncomplexed forms," Infect Immun. (1997) 65(5):1626-30.
Cherkasova et al., "Treatment of Ex Vivo Expanded NK Cells with Daratumumab F(ab')2 Fragments Protects Adoptively Transferred NK Cells from Daratumumab-Mediated Killing and Augments Daratumumab-Induced Antibody Dependent Cellular Toxicity (ADCC) of Myeloma," Blood. (2015) 126(23): 4244.
Chomczynski et al., "Single-step method of RNA isolation by acid guanidinium thiocyanate-phenol-chloroform extraction," Anal Biochem. (1987) 162(1):156-159.
Cooley et al., "First-in-human trial of rhIL-15 and haploidentical natural killer cell therapy for advanced acute myeloid leukemia," Blood Adv. (2019) 3(13):1970-1980.
Cooper et al., "In vivo evidence for a dependence on interleukin 15 for survival of natural killer cells," Blood, 100: 3633-3638 (2002).
Cooper et al., "Memory-like responses of natural killer cells," Immunol. Rev., 235: 297-305 (2010), 14 pages.
De Maria et al., "The impaired NK cell cytolytic function in viremic HIV-1 infection is associated with a reduced surface expression of natural cytotoxicity receptors (NKp46, NKp30 and NKp44)," European Journal of immunology, 33(9): 2410-2418 (2003).
Dempe et al., "Antitumoral activity of parvovirus-mediated IL-2 and MCP-3/CCL7 delivery into human pancreatic cancer: implication of leucocyte recruitment," Cancer Immunol Immunother. (2012) 61(11): 2113-23.
Fauriat et al., "Deficient expression of NCR in NK cells from acute myeloid leukemia: evolution during leukemia treatment and impact of leukemia cells in NCRdull phenotype induction," Blood, 109(1): 323-330 (2007).
Fauriat et al., "Regulation of human NK-cell cytokine and chemokine production by target cell recognition," Blood, 115(11): 2167-2176 (2010).
Finnern et al., "Human autoimmune anti-proteinase 3 scFv from a phage display library," Clin Exp Immunol. (1997) 107(2): 269-81.
Fishwild et al. "High avidity human IgG monoclonal antibodies from novel strains of minilocus transgenic mice." Antibody Engineering II. New Technology, Application & Commercialization (W. Hori, Ed.) (1997): 187-211.
Fishwild et al., "Abstract 1800: Human IgG kappa antigen-specific high affinity monoclonal antibodies from transgenic mice," Faseb Journal, 12(4):A309.
Fishwild et al., "Abstract 753: Human IgG kappa antigen-specific high affinity monoclonal antibodies from transgenic mice," J Allergy Clin Immunol, (1997), 1 page.
Fishwild et al., "High-avidity human IgGK monoclonal antibodies from a novel strain of minilocus transgenic mice," Nature Biotechnology (1996) 14:845-851.
Gappa et al., "The effect of zinc-crystallized glucagon-like peptide-1 on insulin secretion of macroencapsulated pancreatic islets," Tissue Eng. (2001) 7(1): 35-44.
Garcia et al., "Human T cell receptor-mediated recognition of HLA-E," Eur J Immunol. (2002) 32(4): 936-44.
Garcia-Aragoncillo et al., "Design of virotherapy for effective tumor treatment," Curr Opin Mol Ther. (2010) 12(4): 403-11.
GenBank: ABQ28690.1, "CD3zeta chain, partial [*Homo sapiens*]," retrieved online <https://www.ncbi.nlm.nih.gov/protein/ABQ28690.1>, 1 page (2016).
Grayson et al., "Cutting Edge: Increased Expression of Bcl-2 in Antigen-Specific Memory CDS+ T Cells," The Journal of immunology, 164(8): 3950-3954 (2000).
Gujar et al., "Oncolytic virus-initiated protective immunity against prostate cancer," Mol Ther. (2011) 19(4): 797-804.
Guma et al., "Imprint of human cytomegalovirus infection on the NK cell receptor repertoire," Blood, 104: 3664-3671 (2004).
Hallden et al., "Oncolytic virotherapy with modified adenoviruses and novel therapeutic targets," Expert Opin Ther Targets. (2012) 16(10): 945-58.
Hatjiharissi et al., "Increased natural killer cell expression of CD16, augmented binding and ADCC activity to rituximab among individuals expressing the Fc{gamma}RIIIa-158 V/V and V/F polymorphism," Blood. (2007) 110(7): 2561-2564.
Heiber et al., "Vesicular stomatitis virus expressing tumor suppressor p53 is a highly attenuated, potent oncolytic agent," J Virol. (2011) 85(20):10440-50.
Jamieson et al., "Turnover and Proliferation of NK Cells in Steady State and Lymphopenic Conditions," The Journal of immunology, 172(2): 864-870 (2004).
Jarahian et al., "Activation of natural killer cells by newcastle disease virus hemagglutinin-neuraminidase," J Virol. (2009) 83(16): 8108-21.
Jeong et al., "Thermogelling biodegradable copolymer aqueous solutions for injectable protein delivery and tissue engineering," Biomacromolecules. (2002) 3(4):865-8.
Jones et al., "Replacing the complementarity-determining regions in a human antibody with those from a mouse," Nature (1986) 321(6069):522-525.
Kikuchi-Maki et al., "Cutting Edge: KIR2DL4 Transduces Signals into Human NK Cells through Association with the Fc Receptor γ Protein," The Journal of Immunology, 174(7): 3859-3863 (2005).
Kim et al., "FCGR3A gene polymorphisms may correlate with response to frontline R-CHOP therapy for diffuse large B-cell lymphoma," Blood. (2006) 108(8) :2720-2725.
Kim et al., "HLA alleles determine differences in human natural killer cell responsiveness and potency," PNAS, 105(8): 3053-3058 (2008).
Kim et al., "Targeted and armed oncolytic poxviruses: a novel multi-mechanistic therapeutic class for cancer," Nat Rev Cancer. (2009) 9(1): 64-71.
Koene et al., "FcγRIIIa-158V/F Polymorphism Influences the Binding of IgG by Natural Killer Cell FcγRIIIa, Independently of the FcγRIIIa-48L/R/H Phenotype," Blood. (1997) 90(3): 1109-1114.
Kohrt et al., "CD137 stimulation enhances the antilymphoma activity of anti-CD20 antibodies," Blood, 117(8): 2423-2432 (2011).
Kuijpers et al., "Human NK cells can control CMV infection in the absence of T cells," Blood, 112: 914-915 (2008).
Lahiji et al., "Chitosan supports the expression of extracellular matrix proteins in human osteoblasts and chondrocytes," J Biomed Mater Res. (2000) 51(4): 586-95.
Lee et al., "Preparation of poly(vinyl alcohol)-chondroitin sulfate hydrogel as matrices in tissue engineering," Carbohydrate Polymers. (2005) 61:348.

(56) References Cited

OTHER PUBLICATIONS

Lee et al., "The effects of cross-linking of collagen-glycosaminoglycan scaffolds on compressive stiffness, chondrocyte-mediated contraction, proliferation and biosynthesis," Biomaterials. (2001) 22(23): 3145-3154.
Lonberg et al., "Antigen-specific human antibodies from mice comprising four distinct genetic modifications," Nature (1994) 368(6474):856-859.
Lopez-Verges et al., "CD57 defines a functionally distinct population of mature NK cells in the human CD56dimCD16+ NK-cell subset," Blood, 116(19): 3865-3874 (2010).
Magri et al., "NKp46 and DNAM-1 NK-cell receptors drive the response to human cytomegalovirus-infected myeloid dendritic cells overcoming viral immune evasion strategies," Blood, 117: 848-856 (2011).
Mann et al., "Smooth muscle cell growth in photopolymerized hydrogels with cell adhesive and proteolytically degradable domains: synthetic ECM analogs for tissue engineering," Biomaterials. (2001) 22(22): 3045-51.
Marks et al., "By-passing immunization. Human antibodies from V-gene libraries displayed on phage," J Mol Bio (1991) 222(3):581-597.
Mavilio et al., "Natural killer cells in HIV-1 infection: Dichotomous effects of viremia on inhibitory and activating receptors and their functional correlates," PNAS, 100(25): 15011-15016 (2003).
McLoughlin et al., "TNFerade, an adenovector carrying the transgene for human tumor necrosis factor alpha, for patients with advanced solid tumors: surgical experience and long-term follow-up," Ann Surg Oncol. (2005) 12(10):825-30.
Mellor et al., "A critical review of the role of Fc gamma receptor polymorphisms in the response to monoclonal antibodies in cancer," J Hematol Oncol. (2013) 6:1, 10 pages.
Miller et al., "Requirement of an integrated immune response for successful neuroattenuated HSV-1 therapy in an intracranial metastatic melanoma model," Mol Ther. (2003) 7(6):741-7.
Miyamoto et al., "Coxsackievirus B3 is an oncolytic virus with immunostimulatory properties that is active against lung adenocarcinoma," Cancer Res. (2012) 72(10): 2609-21.
Musolino et al., "Immunoglobulin G fragment C receptor polymorphisms and clinical efficacy of trastuzumab-based therapy in patients with HER-2/neu-positive metastatic breast cancer," J Clin Oncol. (2008) 26(11): 1789-1796.
Narni-Mancinelli et al., "Fate mapping analysis of lymphoid cells expressing the NKp46 cell surface receptor," PNAS, 108(45): 18324-18329 (2011).
NCBI Reference Sequence: NP 001018091.1, "killer cell immunoglobulin-like receptor 2DL5B precursor [Homo sapiens]," retrieved online <https://ncbi.nlm.nih.gov/protein/np001018091.1>, 4 pages (2022).
NCBI Reference Sequence: NP 001074239.1, "killer cell immunoglobulin-like receptor 2DL4 isoform c precursor [Homo sapiens]," retrieved online <https://ncbi.nlm.nih.gov/protein/NP001074239.1>, 4 pages (2022).
NCBI Reference Sequence: NP 001074241.1, "killer cell immunoglobulin-like receptor 2DL4 isoform b precursor [Homo sapiens]," retrieved online <https://ncbi.nlm.nih.gov/protein/NP001074241.1>, 4 pages (2022).
NCBI Reference Sequence: NP 001077008.1, "killer cell immunoglobulin-like receptor 3DS1 isoform 1 precursor [Homo sapiens]," retrieved online <https://ncbi.nlm.nih.gov/protein/NP001077008.1>, 5 pages (2022).
NCBI Reference Sequence: NP 001138938.1, "natural cytotoxicity triggering receptor 3 isoform b precursor [Homo sapiens]," retrieved online <https://ncbi.nlm.nih.gov/protein/NP001138938.1>, 4 pages (2022).
NCBI Reference Sequence: NP 001138939.1, "natural cytotoxicity triggering receptor 3 isoform c precursor [Homo sapiens]," retrieved online <https://ncbi.nlm.nih.gov/protein/NP001138939.1>, 4 pages (2022).
NCBI Reference Sequence: NP 001229796.1, "killer cell immunoglobulin-like receptor 3DL2 isoform 2 precursor [Homo sapiens]," retrieved online <https://ncbi.nlm.nih.gov/protein/NP001229796.1>, 5 pages (2023).
NCBI Reference Sequence: NP 002246.5, "killer cell immunoglobulin-like receptor 2DL4 isoform a precursor [Homo sapiens]," retrieved online <https://ncbi.nlm.nih.gov/protein/NP_002246.5>, 4 pages (2022).
NCBI Reference Sequence: NP 004097.1, "high affinity immunoglobulin epsilon receptor subunit gamma precursor [Homo sapiens]," retrieved online <https://ncbi.nlm.nih.gov/protein/NP_004097.1>, 3 pages (2023).
NCBI Reference Sequence: NP 004819.2, "natural cytotoxicity triggering receptor 2 isoform 1 precursor [Homo sapiens]" retrieved online <https://ncbi.nlm.nih.gov/protein/NP_004819.2>, 4 pages (2022).
NCBI Reference Sequence: NP 006728.2, "killer cell immunoglobulin-like receptor 3DL2 isoform 1 precursor [Homo sapiens]," retrieved online <https://ncbi.nlm.nih.gov/protein/NP_006728.2>, 5 pages (2023).
NCBI Reference Sequence: NP 014931.1, "Mpd1 p [Saccharomyces cerevisiae S288c]," retrieved online <https://ncbi.nlm.nih.gov/protein/NP_014931.1>, 2 pages (2011 ).
NCBI Reference Sequence: NP 036444.1, "killer cell immunoglobulin-like receptor 2DS2 isoform a precursor [Homo sapiens]," retrieved online <https://ncbi.nlm.nih.gov/protein/NP_036444.1>, 4 pages (2022).
NCBI Reference Sequence: NP 036445.1, "killer cell immunoglobulin-like receptor 2DS3 precursor [Homo sapiens]," retrieved online <https://ncbi.nlm.nih.gov/protein/NP_036445.1>: 4 pages (2023).
NCBI Reference Sequence: NP 036446.3, "killer cell immunoglobulin-like receptor 2DS4 isoform 1 precursor [Homo sapiens]," retrieved online <https://ncbi.nlm.nih.gov/protein/NP_036446.3>, 5 pages (2023).
NCBI Reference Sequence: NP 037421.2, "killer cell immunoglobulin-like receptor 3DL 1 isoform 1 precursor [Homo sapiens]," retrieved online <https://ncbi.nlm.nih.gov/protein/NP_037421.2>, 5 pages (2023).
NCBI Reference Sequence: NP 055327.1, "killer cell immunoglobulin-like receptor 2DS1 precursor [Homo sapiens]," retrieved online <https://ncbi.nlm.nih.gov/protein/NP_055327.1>, 4 pages (2023).
NCBI Reference Sequence: NP 056952.2, "killer cell immunoglobulin-like receptor 2DL3 precursor [Homo sapiens]," retrieved online <https://ncbi.nlm.nih.gov/protein/NP_056952.2>, 5 pages (2023).
NCBI Reference Sequence: NP 065396.1, "killer cell immunoglobulin-like receptor 2DL5A precursor [Homo sapiens]," retrieved online <https://ncbi.nlm.nih.gov/protein/NP_065396.1>, 4 pages (2023).
NCBI Reference Sequence: NP 076036.1, "INO80 complex subunit B [Mus musculus]," retrieved online <https://ncbi.nlm.nih.gov/protein/NP_076036.1>, 2 pages (2019).
Ogbomo et al., "Tumor cells infected with oncolytic influenza A virus prime natural killer cells for lysis of resistant tumor cells," Med Microbiol Immunol. (2010) 199(2): 93-101.
O'Leary et al., "T cell- and B cell-independent adaptive immunity mediated by natural killer cells," Nature immunology, 7: 507-516 (2006).
Orange., "Formation and function of the lytic NK-cell immunological synapse," Nature Reviews immunology, 8(9): 713-725 (2008), 26 pages.
Parsons et al., "Killer cell immunoglobulin-like receptor 3DL 1 licenses CD16-mediated effector functions of natural killer cells," Journal of Leukocyte Biology, 88(5): 905-912 (2010).
Paust et al., "Critical role for the chemokine receptor CXCR6 in NK cell-mediated antigen specific memory of haptens and viruses," Nature immunology, 11: 1127-1135 (2010).
Pende et al., "Identification and Molecular Characterization of Nkp30, a Novel Triggering Receptor Involved in Natural Cytotoxicity Mediated by Human Natural Killer Cells," Journal of Experimental Medicine, 190(10): 1505-1516 (1999).
Presta, "Antibody engineering," Curr Opin Biotechnol. (1992) 3(4):394-8.
Ranson et al., "IL-15 is an essential mediator of peripheral NK-cell homeostasis," Blood, 101: 4887-4893 (2003).
Ravetch et al. "IgG Fc Receptors," Annu. Rev. Immunol. (2001) 19: 275-290.
Reichmann et al. "Reshaping human antibodies for therapy," Nature (1988) 3 32(6162):323-327.

(56) References Cited

OTHER PUBLICATIONS

Reisfeld et al., "Monoclonal antibodies and cancer therapy," available online at <https://www.osti.gov/biblio/6081141>, (1985), 2 pages. Abstract Only.
Rintoul et al., "ORFV: a novel oncolytic and immune stimulating parapoxvirus therapeutic," Mol Ther. (2012) 20(6): 1148-57.
Saiki et al., "Analysis of enzymatically amplified beta-globin and HLA-DQ alpha DNA with allele-specific oligonucleotide probes," Nature. (1986) 324(6093):163-6.
Sallusto et al., "Two subsets of memory T lymphocytes with distinct homing potentials and effector functions," Nature, 401 :708-712 (1999).
Schlub et al., "Comparing the Kinetics of NK Cells, CD4, and CD8 T Cells in Murine Cytomegalovirus Infection," The Journal of immunology, 187: 1385-1392 (2011).
Shah et al., "Antigen presenting cell-mediated expansion of human umbilical cord blood yields log-scale expansion of natural killer cells with anti-myeloma activity," PLoS One. (2013) 8(10):e76781, 9 pages.
Siegler et al., (2010). "Good manufacturing practice-compliant cell sorting and large-scale expansion of single KIR-positive alloreactive human natural killer cells for multiple infusions to leukemia patients," Cytotherapy, 12:750-763.
Smidsrød et al., "Alginate as immobilization matrix for cells," Trends Biotechnol. (1990) 8(3): 71-78.
Smith, "HLA typing by direct DNA sequencing," Methods Mol Biol. (2012) 882: 67-86.
Somboonyosdech et al., "Correlation of FcγRIIIa polymorphisms and responses to rituximab in Thai population," Asian Biomedicine (2012) 6(6):883-889.
Suggs et al., "Development of poly(propylene fumarate-co-ethylene glycol) as an injectable carrier for endothelial cells," Cell Transplant. (1999) 8(4):345-50.
Suh et al., "Application of chitosan-based polysaccharide biomaterials in cartilage tissue engineering: a review," Biomaterials. (2000) 21(24): 2589-98.
Sun et al., "Adaptive immune features of natural killer cells," Nature, 457: 557-561 (2009), 18 pages.
Tai et al., "Attacking Postoperative Metastases using Perioperative Oncolytic Viruses and Viral Vaccines," Front Oncol. (2014) 4: 217.
Tate et al., "Biocompatibility of methylcellulose-based constructs designed for intracerebral gelation following experimental traumatic brain injury," Biomaterials. (2001) 22(10): 1113-23.
Tomasec et al., "Surface expression of HLA-E, an inhibitor of natural killer cells, enhanced by human cytomegalovirus gpUL40," Science. (2000) 287(5455): 1031.
UniProtKB/Swiss-Pro Reference Sequencet: 095944.2, "RecName: Full=Natural cytotoxicity triggering receptor 2; AltName: Full= Lymphocyte antigen 95 homolog; AltName: Full=NK cell-activating receptor; AltName: Full=Natural killer cell p44-related protein; Short=NK-p44; Short=NKp44; AltName: CD_antigen= CD336; Flags: Precursor," retrieved online <https://ncbi.nlm.nih.gov/protein/O95944.2>, 5 pages (2023).
Verhoyen et al., "Reshaping human antibodies: grafting an antilysozyme activity," Science (1998) 239(4847):1534-1536.
Vivier et al., "Innate or Adaptive Immunity? The Example of Natural Killer Cells," Science, 331 (6013): 44-49 (2011).
White et al., "Characterization of the adaptive and innate immune response to intravenous oncolytic reovirus (Dearing type 3) during a phase I clinical trial," Gene Ther. (2008) 15(12): 911-20.
Yawata et al., "Roles for HLA and KIR polymorphisms in natural killer cell repertoire selection and modulation of effector function," Journal of Experimental Medicine, 203(3): 633-645 (2006).
Yokoyama et al., "How Do Natural Killer Cells Find Self to Achieve Tolerance?," Immunity, 24(3): 249-257 (2006).
Yu et al., "Hierarchy of the Human Natural Killer Cell Response Is Determined by Class and Quantity of Inhibitory Receptors for Self-HLA-B and HLA-C Ligands," The Journal of immunology, 179(9) :5977-5989 (2007).
Zhao et al., "A novel oncolytic herpes simplex virus type 2 has potent anti-tumor activity," PLoS One. (2014) 9(3): e93103, 11 pages.
Zhongguo et al. "Construction of pcDNA3.1(+)/A2E eukaryotic expression vector and its expression on K562 cell," (2005) 13:464-467. (Article in Chinese), English Abstract only.
Biron et al., "Severe Herpesvirus Infections in an Adolescent without Natural Killer Cells," The New England Journal of Medicine, 320: 1731-1735 (1989).
Etzioni et al., "Fatal varicella associated with selective natural killer cell deficiency," The Journal of Pediatrics, 146(3): 423-425 (2005).
Lanier et al., "Co-association of CD3~ with a receptor (CD16) for IgG Fe on human natural killer cells," Nature, 342(6251): 803-805 (1989).
Moretta et al., "Surface NK receptors and their ligands on tumor cells," Seminars in Immunology, 18(3): 151-158 (2006).
ATCC, "NK-92 MI, CRL 2402," Available online at < https://www.atcc.org/products/crl-2408>, 4 pages (2022).
Parham., "Mhc class I molecules and kirs in human history, health and survival," Nature Reviews immunology, 5(3): 201-214 (2005).
Pernick, Handbook of Practical Immunohistochemistry, 2nd Ed., Springer, Table of Contents, 11 pages (2015).
Petersen et al., "Short-term exposure to human cytomegalovirus-infected fibroblasts induces a proportional increase of active CD94/NKG2A+ natural killer cells," Hum. Immunol., 71: 29-35 (2010).
Vivier et al., "Structural similarity between Fe receptors and T cell receptors. Expression of the gamma-subunit of Fe epsilon RI in human T cells, natural killer cells and thymocytes," The Journal of immunology, 147(12): 4263-4270 (1991).

\* cited by examiner

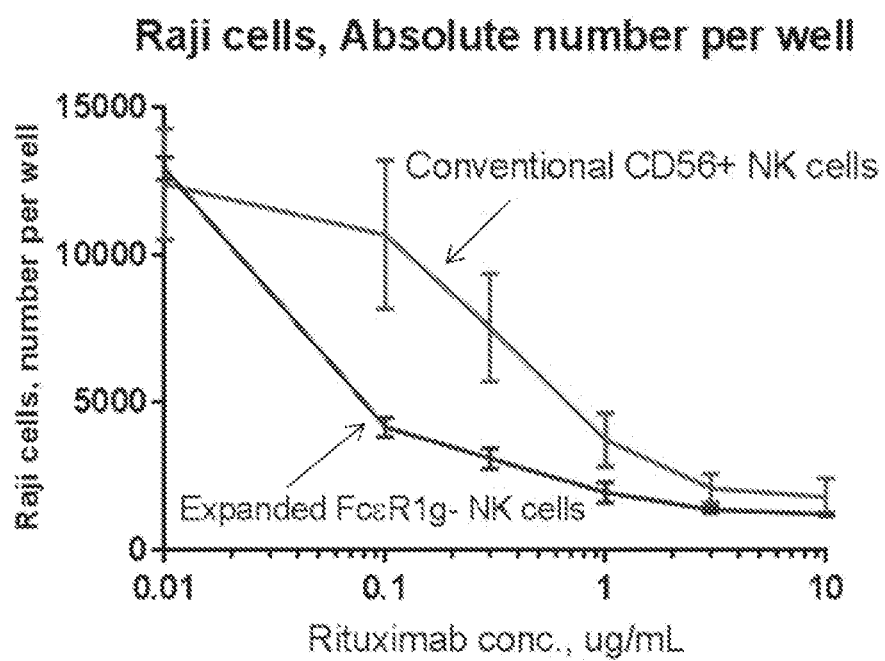

SEQUENCE LISTING

```
<160> NUMBER OF SEQ ID NOS: 6

<210> SEQ ID NO 1
<211> LENGTH: 86
<212> TYPE: PRT
<213> ORGANISM: Homo sapiens
<220> FEATURE:
<223> OTHER INFORMATION: High affinity immunoglobulin gamma Fc receptor
      I
<300> PUBLICATION INFORMATION:
<308> DATABASE ACCESSION NUMBER: NCBI NP-004097.1
<309> DATABASE ENTRY DATE: 2017-12-27

<400> SEQUENCE: 1

Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85
```

-continued

<210> SEQ ID NO 2
<211> LENGTH: 82
<212> TYPE: PRT
<213> ORGANISM: Homo sapiens
<220> FEATURE:
<223> OTHER INFORMATION: CD3zeta
<300> PUBLICATION INFORMATION:
<308> DATABASE ACCESSION NUMBER: NCBI ABQ28690.1
<309> DATABASE ENTRY DATE: 2016-07-23

<400> SEQUENCE: 2

```
Ala Ile Leu Gln Ala Gln Leu Pro Ile Thr Glu Ala Gln Ser Phe Gly
1               5                   10                  15

Leu Leu Asp Pro Lys Leu Cys Tyr Leu Leu Asp Gly Ile Leu Phe Ile
            20                  25                  30

Tyr Gly Val Ile Leu Thr Ala Leu Phe Leu Arg Val Lys Phe Ser Arg
        35                  40                  45

Ser Ala Asp Ala Pro Ala Tyr Gln Gln Gly Gln Asn Gln Leu Tyr Asn
    50                  55                  60

Glu Leu Asn Leu Gly Arg Arg Glu Glu Tyr Asp Val Leu Asp Lys Arg
65                  70                  75                  80

Arg Gly
```

<210> SEQ ID NO 3
<211> LENGTH: 673
<212> TYPE: PRT
<213> ORGANISM: Homo sapiens
<220> FEATURE:
<223> OTHER INFORMATION: PLZF
<300> PUBLICATION INFORMATION:
<308> DATABASE ACCESSION NUMBER: NCBI NP_001018011.1
<309> DATABASE ENTRY DATE: 2017-12-28

<400> SEQUENCE: 3

```
Met Asp Leu Thr Lys Met Gly Met Ile Gln Leu Gln Asn Pro Ser His
1               5                   10                  15

Pro Thr Gly Leu Leu Cys Lys Ala Asn Gln Met Arg Leu Ala Gly Thr
            20                  25                  30

Leu Cys Asp Val Val Ile Met Val Asp Ser Gln Glu Phe His Ala His
        35                  40                  45

Arg Thr Val Leu Ala Cys Thr Ser Lys Met Phe Glu Ile Leu Phe His
    50                  55                  60

Arg Asn Ser Gln His Tyr Thr Leu Asp Phe Leu Ser Pro Lys Thr Phe
65                  70                  75                  80

Gln Gln Ile Leu Glu Tyr Ala Tyr Thr Ala Thr Leu Gln Ala Lys Ala
                85                  90                  95

Glu Asp Leu Asp Asp Leu Leu Tyr Ala Ala Glu Ile Leu Glu Ile Glu
            100                 105                 110

Tyr Leu Glu Glu Gln Cys Leu Lys Met Leu Glu Thr Ile Gln Ala Ser
            115                 120                 125

Asp Asp Asn Asp Thr Glu Ala Thr Met Ala Asp Gly Gly Ala Glu Glu
    130                 135                 140

Glu Glu Asp Arg Lys Ala Arg Tyr Leu Lys Asn Ile Phe Ile Ser Lys
145                 150                 155                 160

His Ser Ser Glu Glu Ser Gly Tyr Ala Ser Val Ala Gly Gln Ser Leu
                165                 170                 175

Pro Gly Pro Met Val Asp Gln Ser Pro Ser Val Ser Thr Ser Phe Gly
            180                 185                 190
```

```
Leu Ser Ala Met Ser Pro Thr Lys Ala Ala Val Asp Ser Leu Met Thr
            195                 200                 205
Ile Gly Gln Ser Leu Leu Gln Gly Thr Leu Gln Pro Pro Ala Gly Pro
        210                 215                 220
Glu Glu Pro Thr Leu Ala Gly Gly Arg His Pro Gly Val Ala Glu
225                 230                 235                 240
Val Lys Thr Glu Met Met Gln Val Asp Glu Val Pro Ser Gln Asp Ser
                245                 250                 255
Pro Gly Ala Ala Glu Ser Ser Ile Ser Gly Met Gly Asp Lys Val
            260                 265                 270
Glu Glu Arg Gly Lys Glu Gly Pro Gly Thr Pro Thr Arg Ser Ser Val
            275                 280                 285
Ile Thr Ser Ala Arg Glu Leu His Tyr Gly Arg Glu Glu Ser Ala Glu
        290                 295                 300
Gln Val Pro Pro Pro Ala Glu Ala Gly Gln Ala Pro Thr Gly Arg Pro
305                 310                 315                 320
Glu His Pro Ala Pro Pro Glu Lys His Leu Gly Ile Tyr Ser Val
                325                 330                 335
Leu Pro Asn His Lys Ala Asp Ala Val Leu Ser Met Pro Ser Ser Val
            340                 345                 350
Thr Ser Gly Leu His Val Gln Pro Ala Leu Ala Val Ser Met Asp Phe
        355                 360                 365
Ser Thr Tyr Gly Gly Leu Leu Pro Gln Gly Phe Ile Gln Arg Glu Leu
        370                 375                 380
Phe Ser Lys Leu Gly Glu Leu Ala Val Gly Met Lys Ser Glu Ser Arg
385                 390                 395                 400
Thr Ile Gly Glu Gln Cys Ser Val Cys Gly Val Glu Leu Pro Asp Asn
                405                 410                 415
Glu Ala Val Glu Gln His Arg Lys Leu His Ser Gly Met Lys Thr Tyr
            420                 425                 430
Gly Cys Glu Leu Cys Gly Lys Arg Phe Leu Asp Ser Leu Arg Leu Arg
        435                 440                 445
Met His Leu Leu Ala His Ser Ala Gly Ala Lys Ala Phe Val Cys Asp
        450                 455                 460
Gln Cys Gly Ala Gln Phe Ser Lys Glu Asp Ala Leu Glu Thr His Arg
465                 470                 475                 480
Gln Thr His Thr Gly Thr Asp Met Ala Val Phe Cys Leu Leu Cys Gly
                485                 490                 495
Lys Arg Phe Gln Ala Gln Ser Ala Leu Gln Gln His Met Glu Val His
            500                 505                 510
Ala Gly Val Arg Ser Tyr Ile Cys Ser Glu Cys Asn Arg Thr Phe Pro
        515                 520                 525
Ser His Thr Ala Leu Lys Arg His Leu Arg Ser His Thr Gly Asp His
        530                 535                 540
Pro Tyr Glu Cys Glu Phe Cys Gly Ser Cys Phe Arg Asp Glu Ser Thr
545                 550                 555                 560
Leu Lys Ser His Lys Arg Ile His Thr Gly Glu Lys Pro Tyr Glu Cys
                565                 570                 575
Asn Gly Cys Gly Lys Lys Phe Ser Leu Lys His Gln Leu Glu Thr His
            580                 585                 590
Tyr Arg Val His Thr Gly Glu Lys Pro Phe Glu Cys Lys Leu Cys His
        595                 600                 605
```

```
Gln Arg Ser Arg Asp Tyr Ser Ala Met Ile Lys His Leu Arg Thr His
    610                 615                 620
Asn Gly Ala Ser Pro Tyr Gln Cys Thr Ile Cys Thr Glu Tyr Cys Pro
625                 630                 635                 640
Ser Leu Ser Ser Met Gln Lys His Met Lys Gly His Lys Pro Glu Glu
                645                 650                 655
Ile Pro Pro Asp Trp Arg Ile Glu Lys Thr Tyr Leu Tyr Leu Cys Tyr
            660                 665                 670
Val
```

<210> SEQ ID NO 4
<211> LENGTH: 238
<212> TYPE: PRT
<213> ORGANISM: Homo sapiens
<220> FEATURE:
<223> OTHER INFORMATION: CD16 (158F)

<400> SEQUENCE: 4

```
Gly Met Arg Thr Glu Asp Leu Pro Lys Ala Val Val Phe Leu Glu Pro
1               5                   10                  15
Gln Trp Tyr Arg Val Leu Glu Lys Asp Ser Val Thr Leu Lys Cys Gln
            20                  25                  30
Gly Ala Tyr Ser Pro Glu Asp Asn Ser Thr Gln Trp Phe His Asn Glu
        35                  40                  45
Ser Leu Ile Ser Ser Gln Ala Ser Ser Tyr Phe Ile Asp Ala Ala Thr
    50                  55                  60
Val Asp Asp Ser Gly Glu Tyr Arg Cys Gln Thr Asn Leu Ser Thr Leu
65                  70                  75                  80
Ser Asp Pro Val Gln Leu Glu Val His Ile Gly Trp Leu Leu Leu Gln
                85                  90                  95
Ala Pro Arg Trp Val Phe Lys Glu Glu Asp Pro Ile His Leu Arg Cys
            100                 105                 110
His Ser Trp Lys Asn Thr Ala Leu His Lys Val Thr Tyr Leu Gln Asn
        115                 120                 125
Gly Lys Gly Arg Lys Tyr Phe His His Asn Ser Asp Phe Tyr Ile Pro
    130                 135                 140
Lys Ala Thr Leu Lys Asp Ser Gly Ser Tyr Phe Cys Arg Gly Leu Phe
145                 150                 155                 160
Gly Ser Lys Asn Val Ser Ser Glu Thr Val Asn Ile Thr Ile Thr Gln
                165                 170                 175
Gly Leu Ala Val Ser Thr Ile Ser Ser Phe Phe Pro Pro Gly Tyr Gln
            180                 185                 190
Val Ser Phe Cys Leu Val Met Val Leu Leu Phe Ala Val Asp Thr Gly
        195                 200                 205
Leu Tyr Phe Ser Val Lys Thr Asn Ile Arg Ser Ser Thr Arg Asp Trp
    210                 215                 220
Lys Asp His Lys Phe Lys Trp Arg Lys Asp Pro Gln Asp Lys
225                 230                 235
```

<210> SEQ ID NO 5
<211> LENGTH: 16
<212> TYPE: PRT
<213> ORGANISM: Homo sapiens
<220> FEATURE:
<223> OTHER INFORMATION: CD16 (158F) signal peptide

```
<400> SEQUENCE: 5

Met Trp Gln Leu Leu Leu Pro Thr Ala Leu Leu Leu Val Ser Ala
1               5                   10                  15

<210> SEQ ID NO 6
<211> LENGTH: 238
<212> TYPE: PRT
<213> ORGANISM: Homo sapiens
<220> FEATURE:
<223> OTHER INFORMATION: CD16 (158V)

<400> SEQUENCE: 6

Gly Met Arg Thr Glu Asp Leu Pro Lys Ala Val Val Phe Leu Glu Pro
1               5                   10                  15

Gln Trp Tyr Arg Val Leu Glu Lys Asp Ser Val Thr Leu Lys Cys Gln
            20                  25                  30

Gly Ala Tyr Ser Pro Glu Asp Asn Ser Thr Gln Trp Phe His Asn Glu
        35                  40                  45

Ser Leu Ile Ser Ser Gln Ala Ser Ser Tyr Phe Ile Asp Ala Ala Thr
    50                  55                  60

Val Asp Asp Ser Gly Glu Tyr Arg Cys Gln Thr Asn Leu Ser Thr Leu
65                  70                  75                  80

Ser Asp Pro Val Gln Leu Glu Val His Ile Gly Trp Leu Leu Leu Gln
                85                  90                  95

Ala Pro Arg Trp Val Phe Lys Glu Glu Asp Pro Ile His Leu Arg Cys
            100                 105                 110

His Ser Trp Lys Asn Thr Ala Leu His Lys Val Thr Tyr Leu Gln Asn
        115                 120                 125

Gly Lys Gly Arg Lys Tyr Phe His His Asn Ser Asp Phe Tyr Ile Pro
    130                 135                 140

Lys Ala Thr Leu Lys Asp Ser Gly Ser Tyr Phe Cys Arg Gly Leu Val
145                 150                 155                 160

Gly Ser Lys Asn Val Ser Ser Glu Thr Val Asn Ile Thr Ile Thr Gln
                165                 170                 175

Gly Leu Ala Val Ser Thr Ile Ser Ser Phe Phe Pro Pro Gly Tyr Gln
            180                 185                 190

Val Ser Phe Cys Leu Val Met Val Leu Leu Phe Ala Val Asp Thr Gly
        195                 200                 205

Leu Tyr Phe Ser Val Lys Thr Asn Ile Arg Ser Ser Thr Arg Asp Trp
    210                 215                 220

Lys Asp His Lys Phe Lys Trp Arg Lys Asp Pro Gln Asp Lys
225                 230                 235
```

ENGINEERED NATURAL KILLER (NK) CELLS AND COMPOSITIONS AND METHODS THEREOF

CROSS-REFERENCE TO RELATED APPLICATIONS

This application is a National Stage application under 35 U.S.C. § 371 of International Application No. PCT/US2018/017493, filed on Feb. 8, 2018, which claims priority from U.S. provisional application No. 62/457,098 filed Feb. 9, 2017, entitled "ENGINEERED NATURAL KILLER (NK) CELLS AND COMPOSITIONS AND METHODS THEREOF," and U.S. provisional application No. 62/484,350 filed Apr. 11, 2017, entitled "ENGINEERED NATURAL KILLER (NK) CELLS AND COMPOSITIONS AND METHODS THEREOF," the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 776032000100SeqList.txt, created Aug. 6, 2019, which is 12,177 bytes in size. The information in the electronic format of the Sequence Listing is incorporated by reference in its entirety.

FIELD OF THE INVENTION

The present invention provides engineered Natural Killer (NK) cells and methods of producing engineered NK cells. The engineered NK cells and compositions containing the engineered NK cells are useful for treating diseases such as cancer.

BACKGROUND OF THE INVENTION

NK cells were discovered 40 years ago by their ability to recognize and kill tumor cells without the requirement of prior antigen exposure. Since then, NK cells have been seen as promising agents for cell based cancer therapy. Most cancers lack identifiable, tumorspecific antigens in the HLA context, and thus cannot succumb to antigen specific cytotoxic T lymphocytes. Since a wide range of cancer cells are sensitive to NK cytotoxicity, one major advantage of using NK cells is that transplantation of natural killer (NK) cell can be employed against cancer cells in an allogeneic setting, without risk of graft-versus-host disease. The therapeutic promise of NK cells has been limited by the difficulty in obtaining a theoretically effective amount of NK cells, particularly NK cells that exhibit cytotoxic effector functions for killing malignant tumor cells or infected cells. Accordingly, there is a need for engineered NK cells for therapeutic use. Provided herein are embodiments that meet such needs.

BRIEF SUMMARY OF THE INVENTION

Provided herein are engineered natural killer (NK) cells that have reduced expression, activity and/or signaling of the FcRγ chain. In some embodiments, the provided engineered cells exhibit enhanced immune responses, including for the treatment of cancer, microbial infections and/or viral infections in a subject. Also provided are methods of treatment of a subject by administering a therapeutically effective amount of the provided engineered NK cells. In some embodiments, the engineered NK cells are useful for enhancing therapeutic responses to an administered therapeutic antibody, such as to an anti-cancer, anti-viral or anti-microbial monoclonal antibody.

In some embodiments, provided herein is an engineered NK cell, wherein the NK cell is genetically engineered to reduce FcRγ chain expression, activity and/or signaling in the cell. In some of these embodiments, the engineered NK cell comprises a genetic disruption of a gene resulting in reduced FcRγ chain expression, activity and/or signaling in the cell. In some cases, the genetic disruption can result in a deletion or mutation of the gene. In some embodiments, the engineered NK cell comprises an inhibitory nucleic acid that reduces expression of a gene that results in reduced FcRγ chain expression, activity and/or signaling in the cell.

In some embodiments, the engineered NK cell comprises a genetic disruption of a gene encoding FcRγ chain and/or a genetic disruption resulting in reduced expression of FcRγ chain in the engineered NK cell. In some embodiments, the engineered NK cell comprises a genetic disruption of a gene encoding a protein regulating expression or activity of FcRγ chain and/or a genetic disruption resulting in reduced expression of a protein regulating expression or activity of FcRγ chain. In some embodiments, the engineered NK cell comprises a genetic disruption of a gene encoding a protein involved in FcRγ chain-dependent signaling and/or a genetic disruption resulting in reduced expression of a protein involved in FcRγ chain-dependent signaling. In some embodiments, the engineered cell can contain one or more of the above genetic disruptions. In some embodiments, the genetic disruption comprises a deletion, mutation and/or insertion resulting in a premature stop codon in the gene or a frameshift of the open reading frame of the gene. In some embodiments, both alleles of the gene encoding FcRγ chain, the gene encoding a protein regulating expression or activity of FcRγ chain and/or the gene encoding a protein involved in FcRγ chain-dependent signaling are disrupted in the engineered NK cells.

In some embodiments, the engineered NK cell comprises an inhibitory nucleic acid molecule targeting a gene in the NK cell resulting in reduced expression of FcRγ chain, reduced expression of a protein regulating expression or activity of FcRγ chain and/or reduced expression of a protein involved in FcRγ chain-dependent signaling. In some embodiments, the inhibitory nucleic acid interferes with or reduces expression of a gene encoding FcRγ chain, a gene encoding a protein regulating expression or activity of FcRγ chain and/or a gene encoding a protein involved in FcRγ chain-dependent signaling. In some embodiments, the inhibitory nucleic acid comprises an RNA interfering agent. In some embodiments, the inhibitory nucleic acid comprises siRNA, shRNA, or miRNA.

In some of any such embodiments, the expression of FcRγ chain, a protein regulating expression or activity of FcRγ chain and/or a protein involved in FcRγ chain-dependent signaling is reduced by greater than or greater than about 50%, 60%, 70%, 80%, 90%, or 95% in the engineered NK cell as compared to the expression of the protein in the NK cell that is not genetically engineered.

In some of any such embodiments, expression of a protein regulating expression or activity of FcRγ chain is reduced in the engineered NK cell. In some of these embodiments, the protein regulating expression or activity of FcRγ chain is a transcription factor. In some embodiments, the transcription factor is PLZF (ZBTB16) or HELIOS (IKZF2).

In some of any such embodiments, the expression of a protein involved in FcRγ chain-dependent signaling is reduced in the engineered NK cell. In some embodiments, the protein involved in FcRγ chain-dependent signaling is a downstream signaling molecule of FcRγ. In some of these embodiments, the downstream signaling molecule is SYK, DAB2 or EAT-2.

In some of any such embodiments, expression of FcRγ chain is reduced in the engineered NK cell. In some embodiments, the engineered NK cell comprises a genetic disruption in a gene encoding FcRγ chain. In some of these embodiments, the genetic disruption comprises a deletion, mutation and/or insertion resulting in a premature stop codon in the gene or a frameshift of the open reading frame of the gene. In some embodiments, both alleles of the gene encoding FcRγ chain are disrupted in the genome of the engineered NK cell. In some embodiments, the engineered NK cell comprises an inhibitory nucleic acid molecule that targets a gene encoding FcRγ chain, thereby reducing expression of FcRγ chain in the cell. In some embodiments, the inhibitory nucleic acid molecule comprises a sequence complementary to the gene encoding FcRγ chain. In some embodiments, the inhibitory nucleic acid comprises an RNA interfering agent In some embodiments, the inhibitory nucleic acid comprises siRNA, shRNA, or miRNA. In some embodiments, the expression of FcRγ chain is reduced by greater than or greater than about 50%, 60%, 70%, 80%, 90%, or 95% in the engineered NK cell as compared to the expression in the NK cell that is not genetically engineered.

In some of any of the provided embodiments, the reduced FcRγ chain expression, activity and/or signaling in the engineered NK cell is permanent, transient or inducible. In some embodiments, the expression, activity and/or signaling of FcRγ chain is reduced by greater than or greater than about 50%, 60%, 70%, 80%, 90%, or 95% as compared to the expression, activity and/or signaling in the NK cell that is not genetically engineered. In some embodiments, the expression of FcRγ chain expressed in the cell is undetectable in an immunoblot assay.

In some of any of the embodiments, the engineered NK cell is derived from a primary cell obtained from a subject. In some embodiments, the subject is human.

In some of any of the embodiments, the engineered NK cell is derived from a clonal cell line. In some embodiments, the clonal cell line is NK-92, NK-YS, KHYG-1, NKL, NKG, SNK-6, or IMC-1.

In some of any of the embodiments, CD16 is expressed on the surface of the engineered NK cell. In some of any of the embodiments, the engineered NK cell expresses CD3-zeta (CD3ζ) chain. In some embodiments, the expressed CD16 and/or CD3ζ chain is endogenous to the NK cell. In some embodiments, the engineered NK cell is additionally engineered to express a recombinant or heterologous CD16 and/or CD3ζ chain in the NK cell. In some embodiments, the engineered NK cell comprises a recombinant or heterologous CD16 gene and/or a recombinant or heterologous CD3-zeta (CD3ζ) chain. In some embodiments, the recombinant or heterologous CD16 comprises a CD16-activating mutation. In some embodiments, the CD16 activating mutation is a mutation that results in higher affinity to IgG1. In some embodiments, the CD16 comprises the mutation 158V. In some embodiments, the CD16 comprises the mutation 158F.

Also provided are engineered NK cells that have reduced surface expression of an NK inhibitory receptor. In some embodiments, any of the provided engineered NK cells that have reduced expression, activity and/or signaling of FcRγ chain can additionally have reduced surface expression on an NK inhibitory receptor. In some embodiments, the engineered NK cells comprises a genetic disruption of a gene encoding a NK inhibitory receptor and/or a genetic disruption resulting in reduced expression of an NK inhibitory receptor. In some embodiments, the engineered NK cell comprises an inhibitory nucleic acid that targets a gene encoding a gene encoding an NK inhibitory receptor and/or results in reduced expression of an NK inhibitory receptor in the cell. In some embodiments, the inhibitory receptor is NKG2A and/or KIR2DL1. In some embodiments, expression of the inhibitory receptor, such as NKG2A and/or KIR2DL1, is reduced by greater than or greater than about 50%, 60%, 70%, 80%, 90%, or 95% as compared to the expression, activity and/or signaling in the NK cell that is not genetically engineered.

In some embodiments, the engineered NK cell exhibits increased activity when stimulated through CD16 compared to the NK cell that is not genetically engineered. In some embodiments, the increased activity is observed following CD16 engagement by CD16 crosslinking, such as can occur in the presence of an antibody by binding of the Fc portion of the antibody to CD16.

In some embodiments, the engineered NK cell has reduced surface expression of NKp46, NKp30, and/or NKp44 compared to the NK cell without the modification. In some embodiments, expression of NKp46, NKp30, and/or NKp44 is reduced in the cell by greater than or greater than about 20%, 30%, 40%, 50%, 60%, 70%, 80%, 90%, 95% or more compared to the expression in the NK cell that is not genetically engineered.

Also provided herein is a method of producing an engineered NK cell, comprising genetically engineering the NK cell to reduce FcRγ chain expression, activity, and/or signaling in the cell. In some of these embodiments, the methods involve disrupting a gene or repressing expression a gene to effect reduced FcRγ chain expression, activity and/or signaling in the cell. In some cases, the genetic disruption can result in a deletion or mutation of the gene. In some embodiments, the methods involves introducing into the cell an inhibitory nucleic acid that reduces expression of a gene that results in reduced FcRγ chain expression, activity and/or signaling in the cell.

In some embodiments, the method comprises disrupting a gene encoding FcRγ chain and/or disrupting a gene that results in reduced expression of FcRγ chain in the engineered NK cell. In some embodiments, the method comprises disrupting a gene encoding a protein regulating expression or activity of FcRγ chain and/or a disrupting a gene that results in reduced expression of a protein regulating expression or activity of FcRγ chain. In some embodiments, the method comprises disrupting a gene encoding a protein involved in FcRγ chain-dependent signaling and/or a disrupting a gene that results in reduced expression of a protein involved in FcRγ chain-dependent signaling. In some embodiments, the method of disrupting the gene results in introducing a deletion, mutation, or insertion into the gene.

In some embodiments, the method of disrupting the gene comprises introducing into an NK cell an endonuclease that has been engineered to target to the gene. In some embodiments, the endonuclease is a TAL nuclease, meganuclease, zinc-finger nuclease, CRISPR-associated protein 9 (Cas9), or Argonaute. In some embodiments, the endonuclease is a Cas9 that is a fusion with or is complexed with at least one guide RNA that is complementary with a target domain or region of the gene. In some embodiments, the Cas9 is an S.

aureus Cas9 molecule. In some embodiments, the Cas9 molecule is an *S. pyogenes* Cas9. In some embodiments, the method involves introducing into the cell an endonuclease, such as Cas9, that targets to the gene encoding FcRγ chain in the NK cell.

In some embodiments, the method for repressing expression of a gene comprises introducing an inhibitory nucleic acid into the cell that targets a gene to result in reduced FcRγ chain expression, activity and/or signaling in the cell. In some embodiments, one or more inhibitory nucleic acid molecule is introduced into the cell that targets one or more genes resulting in reduced expression of a gene encoding FcRγ chain, a gene encoding a protein regulating expression or activity of FcRγ chain and/or a gene encoding a protein involved in FcRγ chain-dependent signaling. In some embodiments, the inhibitory nucleic acid comprises a sequence complementary to a gene encoding FcRγ chain. In some embodiments, the inhibitory nucleic acid comprises a sequence complementary to a gene encoding a protein regulating expression or activity of FcRγ chain. In some embodiments, the inhibitory nucleic acid comprises a sequence complementary to a gene encoding a protein involved in FcRγ chain-dependent signaling. In some embodiments, the inhibitory nucleic acid comprises an RNA interfering agent. In some embodiments, the nucleic acid is siRNA, shRNA, or miRNA.

In some of any such embodiments, the method is carried out to reduce expression of a protein regulating expression or activity of FcRγ chain in the NK cell. In some of these embodiments, the protein regulating expression or activity of FcRγ chain is a transcription factor. In some embodiments, the transcription factor is PLZF (ZBTB16) or HELIOS (IKZF2).

In some of any such embodiments, the method is carried out to reduce expression of a protein involved in FcRγ chain-dependent signaling in the NK cell. In some embodiments, the protein involved in FcRγ chain-dependent signaling is a downstream signaling molecule of FcRγ. In some of these embodiments, the downstream signaling molecule is SYK, DAB2 or EAT-2.

In some of any such embodiments, the method is carried out to reduce expression of FcRγ chain in the NK cell.

In some of any of the embodiments, the method is carried out in vitro. In some of any of the embodiments, the method is carried out ex vivo, such as from cells isolated from a subject, such as from a human patient. In some of any of the embodiments, the method is carried so that the reduced expression is permanent, transient, or inducible.

In some embodiments, the methods for producing an engineered NK cell involves carrying out the genetic engineering, such as the disruption or repression of expression of a gene as described, in primary NK cells obtained from a subject. In some embodiments, the subject is mammalian, such as is human.

In some embodiments, prior to disrupting or repressing expression of the gene, the method comprises (i) isolating a NK cell from a sample from a mammalian subject. In some embodiments, the mammalian subject is human. In some of these embodiments, the sample comprises peripheral blood mononuclear cells (PBMC). In some embodiments, isolating the NK cell comprises selecting NK cells based on surface expression of an NK cell marker. In some embodiments, the NK cell marker is one or more of CD56, CD161, KIR, NKG2A, NKG2D, NKp30, NKp44, NKp46, 2B4, NTB-A, CRACC, DNAM-1, CD69, and/or CD25. In some embodiments, the method comprises selecting NK cells from other lymphocytes by selecting cells that do not express surface CD3, a T-cell antigen receptor (TCR) and/or surface immunoglobulins (Ig) B cell receptor. In some embodiments, the NK cells are selected or are additionally selected to have surface expression of CD16. In some embodiments, the NK cells express CD3ζ.

In some embodiments, the methods for producing an engineered NK cell involves carrying out the genetic engineering on an NK cell line. In some embodiments, the cell line is NK-92, NK-YS, KHYG-1. NKL, NKG, SNK-6, or IMC-1.

In some embodiments, the method comprises engineering the NK cell line to express a recombinant or heterologous CD16 and/or CD3ζ. In some embodiments, the method comprises introducing into the NK cell a nucleic acid encoding the CD16 and/or CD3ζ. In some embodiments, the recombinant or heterologous CD16 contains an activating mutation. In some embodiments, the activating mutation increases affinity of CD16 for IgG. In some embodiments, the CD16 comprises a 158V mutation. In some embodiments, the CD16 comprises a 158F mutation.

In some embodiments, the method comprises virally transducing the NK cell with nucleic acid encoding the CD16 and/or CD3ζ gene. In some embodiments, the method comprises transfecting the NK cell with nucleic acid encoding the CD16 and/or CD3ζ gene. In some embodiments, the method comprises transiently, inducibly, or permanently expressing CD16 or CD3ζ in the NK cell.

In some embodiments, the method is carried out so that FcRγ chain expression, signaling and/or activity is reduced in the NK cell by greater than or greater than about 50%, 60%, 70%, 80%, 90%, or 95% as compared to the expression in the NK cell that is not genetically engineered by the present method. In some embodiments, the FcRIγ adaptor protein expression level is not detectable by an immunoblot assay.

Also provided is a method of producing an engineered NK cell that has reduced surface expression of an NK inhibitory receptor. In some embodiments, any of the provided methods for producing an engineered NK cell that have reduced expression, activity and/or signaling of FcRγ chain can additionally involve reducing surface expression on an NK inhibitory receptor. In some embodiments, such engineered NK cells are produced by a method that includes disrupting a gene encoding a NK inhibitory receptor. In some embodiments, such engineered NK cells are producing by introducing into the NK cell an inhibitory nucleic acid that targets a gene encoding an NK inhibitory receptor. In some embodiments, the inhibitory receptor is NKG2A and/or KIR2DL1. In some embodiments, such methods are carried out so that expression of an NK inhibitory receptor, such as NKG2A and/or KIR2DL1, is reduced in the NK cell by greater than or greater than about 50%, 60%, 70%, 80%, 90%, or 95% as compared to the expression of the inhibitory receptor in the NK cell that is not genetically engineered by the present method.

In some embodiments, the provided methods for producing genetically engineered NK cell can further include a step of expanding the engineered NK cells. In some embodiments, expanding the engineered NK cells involves culturing or incubating the engineered NK cells in the presence of feeder cells or cytokines. In some embodiments, expanding the engineered NK cells in carried out in vitro. In some embodiments, expanding the engineered NK cells is carried out in vivo.

Also provided are engineered NK cells produced by any of the above methods.

Also provided herein are compositions comprising any of the provided engineered NK cells. In one embodiment, the composition comprises a therapeutically effective amount of the engineered NK cells provided herein and a pharmaceutically acceptable carrier. In some embodiments, the carrier is a saline solution, a dextrose solution, or 5% human serum albumin. In some embodiments, the composition comprises between $1\times10^5$ and $1\times10^8$ cells/mL.

In some embodiments, the composition is a cryopreserved composition and/or comprises the engineered NK cells and a cryoprotectant.

Also provided here are kits comprising an engineered NK cell and an additional agent. In some embodiments, the kits further comprise instructions for use, for example, instructions for administering the engineered NK cell and additional agent for treatment of a disease. In some embodiments, the additional agent is an antibody or an Fc-fusion protein. In some embodiments, the antibody recognizes a tumor associated antigen, a viral antigen, a microbial antigen. In some embodiments, the antibody is selected from the group consisting of an anti-CD20 antibody, an anti-HER2 antibody, an anti-CD52 antibody, an anti-EGFR antibody and an anti-CD38 antibody. In some embodiments, the antibody comprises an Fc domain.

Also provided herein is a method of treating a condition comprising administering any of the provided engineered NK cells to an individual in need thereof. In some embodiments, the individual is a mammalian subject, such as a human subject. In some embodiments, the subject is one that has a cancer or an infection, such as a viral infection or microbial infection. In some embodiments, the method comprises administering $1\times10^8$ to $1\times10^{10}$ cells/m$^2$ to the individual.

In some embodiments, the provided methods further include administering an additional agent. In some embodiments, the additional agent is an antibody or an Fc-fusion protein. In some embodiments, the antibody recognizes a tumor associated antigen, a viral antigen, a microbial antigen. In some embodiments, the antibody is an anti-CD20 antibody, an anti-HER2 antibody, an anti-CD52 antibody, an anti-EGFR antibody or an anti-CD38 antibody. In some embodiments, the antibody comprises an Fc domain.

In some embodiments, the additional agent and the engineered NK cells are administered sequentially. In some embodiments, the additional agent is administered prior to administration of the engineered NK cells. In some embodiments, the additional agent and the engineered NK cells are administered simultaneously.

In some embodiments, the method comprises administering NK cells to treat an inflammatory condition, an infection, and/or cancer. In some embodiments, the infection is a viral infection or a bacterial infection. In some embodiments, the cancer is leukemia or lymphoma. In some embodiments, the individual expresses a low affinity FcγRIIIA. In some embodiments, the individual is a human.

In some embodiments, the engineered NK cell is allogenic to the subject. In some embodiments, the engineered NK cell is autologous to the subject.

BRIEF DESCRIPTION OF THE DRAWINGS

FIG. 1 depicts activity of g-NK cells and conventional NK cells in an antibody dependent cell cytotoxicity (ADCC) assay in the absence or presence of anti-CD20 antibody Rituximab.

DETAILED DESCRIPTION OF THE INVENTION

Provided herein are engineered Natural Killer (NK) cells that are genetically engineered to have reduced expression, activity and/or signaling of the FcRγ (also known as FcεRIγ). In some aspects, the provided engineered NK cells are genetically engineered to knockout (e.g. by genetic disruption) or knockdown (e.g. by gene silencing or repression) a gene encoding FcRγ, a gene encoding a protein controlling expression of the FcRγ, such as a transcription factor, or a gene encoding a protein involved in FcRγ-dependent signaling, such as a downstream signaling molecule of FcRγ.

Natural killer (NK) cells are innate lymphocytes important for mediating anti-viral and anti-cancer immunity through cytokine and chemokine secretion, and through the release of cytotoxic granules (Vivier et al. Science 331 (6013):44-49 (2011); Caligiuri, Blood 112(3):461-469 (2008); Roda et al., Cancer Res. 66(1):517-526 (2006)). NK cells are effector cells that comprise the third largest population of lymphocytes and are important for host immunosurveillance against tumor and pathogen-infected cells.

However, unlike T and B lymphocytes, N K cells are thought to have only a limited capacity for target recognition using germline-encoded activation receptors (Bottino et al., Curr Top Microbiol Immunol. 298:175-182 (2006); Stewart et al., Curr Top Microbiol Immunol. 298:1-21 (2006)). Instead, NK cells express the activating Fc receptor CD16, which recognizes IgG-coated target cells, thereby broadening target recognition (Ravetch & Bolland, Annu Rev Immunol. 19:275-290 (2001); Lanier Nat. Immunol. 9(5):495-502 (2008); Bryceson & Long. Curr Opin Immunol. 20(3):344-352 (2008)). In some cases, antibody-dependent cellular cytotoxicity (ADCC) is triggered when receptors on the NK cell surface (such as CD16) recognize IgG1 or IgG3 antibodies bound to the surface of a cell. This triggers release of cytoplasmic granules containing perforin and granzymes, leading to target cell death. ADCC and antibody-dependent cytokine/chemokine production are primarily mediated by NK cells.

In some cases, ADCC is a mechanism of action of therapeutic antibodies, including anti-cancer antibodies. While significant advances have been made in cancer treatment by use of antibodies directed against cancer antigens, the responsiveness of patients to such antibodies varies. Investigation of such variable responses has typically focused on the direct inhibitory effects of these antibodies on the tumor cells (e.g. inhibition of growth factor receptors and the subsequent induction of apoptosis) and the in vivo effects of these antibodies may be more complex and may involve the host immune system, including through ADCC. In some aspects, cell therapy by administering NK cells can be used in concert with antibodies for therapeutic and related purposes.

Upon activation. NK cells produce cytokines and chemokines abundantly and at the same time exhibit potent cytolytic activity. Activation of NK cells can occur through the direct binding of NK cell receptors to ligands on the target cell, as seen with direct tumor cell killing, or through the crosslinking of the Fc receptor (CD 16; FcγRIII) by binding to the Fc portion of antibodies bound to an antigen-bearing cell. The expression and signal transduction activity of several NK cell activation receptors requires physically associated adaptors, which transduce signals through immunoreceptor tyrosine-based activation motifs (ITAMs). Among these adaptors. FcRγ and CD3ζ chains can associate with CD16 and natural cytotoxicity receptors (NCRs) as either disulfide-linked homo-dimers or hetero-dimers, and these chains have been thought to be expressed by all mature NK cells.

In some aspects, CD16 engagement (CD16 crosslinking) initiates NK cell responses via intracellular signals that are generated through one, or both, of the CD16-associated adaptor chains, FcRγ or CD3ζ. Triggering of CD16 leads to phosphorylation of the γ or ζ chain, which in turn recruits tyrosine kinases, syk and ZAP-70, initiating a cascade of signal transduction leading to rapid and potent effector functions. The most well-known effector function is the release of cytoplasmic granules carrying toxic proteins to kill nearby target cells through the process of antibody-dependent cellular cytotoxicity. CD16 crosslinking also results in the production of cytokines and chemokines that, in turn, activate and orchestrate a series of immune responses.

This release of cytokines and chemokines can play a role in the anti-cancer activity of NK cells in vivo. NK cells also have small granules in their cytoplasm containing perforin and proteases (granzymes). Upon release from the NK cell, perforin forms pores in the cell membrane of targeted cells through which the granzymes and associated molecules can enter, inducing apoptosis. The fact that NK cells induce apoptosis rather than necrosis of target cells is significant-necrosis of a virus-infected cell would release the virions, whereas apoptosis leads to destruction of the virus inside the cells.

The provided engineered NK cells include cells that are engineered to have lower activity or expression of FcRγ signaling adaptor. In some cases, the engineered cells express the signaling adaptor CD3ζ-chain abundantly, but are deficient in the expression of the signaling adaptor FcRγ-chain. In some embodiments, compared to NK cells that express the signaling adaptor FcRγ-chain, these engineered NK cells exhibit dramatically enhanced activity when activated by engagement of CD16, such as can occur in the presence of antibodies. For example, the engineered cells can be activated by antibody-mediated crosslinking of CD16 or by antibody-coated tumor cells. Also provided are methods of producing the engineered cells. The provided engineered NK cells and methods address problems related to selecting or identifying NK cells of a particular phenotype, which may only be present as a small percentage of total NK cells in a subject and/or which may not normally exist in all subjects in a population. In some aspects, the provided embodiments offer an improved NK cell therapy in which NK cells can be engineered with enhanced activities and yet can be more easily obtained in sufficient amounts for therapeutic use, including for administration in concert with antibodies, compared to NK cells of a similar phenotype isolated directly from a subject.

All references cited herein, including patent applications, patent publications, and scientific literature and databases, are herein incorporated by reference in their entirety for all purposes to the same extent as if each individual reference were specifically and individually indicated to be incorporated by reference.

For clarity of disclosure, and not by way of limitation, the detailed description is divided into the subsections that follow. The section headings used herein are for organizational purposes only and are not to be construed as limiting the subject matter described.

I. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, "antibody" refers to immunoglobulins and immunoglobulin fragments, whether natural or partially or wholly synthetically, such as recombinantly, produced, including any fragment thereof containing at least a portion of the variable heavy chain and/or light chain region of the immunoglobulin molecule that is sufficient to form an antigen binding site and, when assembled, to specifically bind antigen. Hence, an antibody includes any protein having a binding domain that is homologous or substantially homologous to an immunoglobulin antigen-binding domain (antibody combining site). Typically, antibodies minimally include all or at least a portion of the variable heavy ($V_H$) chain and/or the variable light ($V_L$) chain. In general, the pairing of a $V_H$ and $V_L$ together form the antigen-binding site, although, in some cases, a single $V_H$ or $V_L$ domain is sufficient for antigen-binding. The antibody also can include all or a portion of the constant region. Reference to an antibody herein includes full-length antibody and antigen-binding fragments. The term "immunoglobulin" (Ig) is used interchangeably with "antibody" herein.

The terms "full-length antibody," "intact antibody" or "whole antibody" are used interchangeably to refer to an antibody in its substantially intact form, as opposed to an antibody fragment. A full-length antibody is an antibody typically having two full-length heavy chains (e.g., VH-CH1-CH2-CH3 or VH-CH1-CH2-CH3-CH4) and two full-length light chains (VL-CL) and hinge regions, such as antibodies produced from mammalian species (e.g. human, mouse, rat, rabbit, non-human primate, etc.) by antibody secreting B cells and antibodies with the same domains that are produced synthetically. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Antibody fragments, include, but are not limited to, Fab fragments, Fab' fragments, F(ab')$_2$ fragments. Fv fragments, disulfide-linked Fvs (dsFv), Fd fragments. Fd' fragments; diabodies; linear antibodies (see U.S. Pat. No. 5,641,870, Example 2; Zapata et al., *Protein Eng.* 8(10): 1057-1062 [1995]); single-chain antibody molecules, including single-chain Fvs (scFv) or single-chain Fabs (scFab); antigen-binding fragments of any of the above and multispecific antibodies from antibody fragments. For purposes herein, an antibody fragment typically includes one that is sufficient to engage or crosslink CD16 on the surface of an NK cell.

The term "autologous" refers to cells or tissues originating within or taken from an individual's own tissues. For example, in an autologous transfer or transplantation of NK cells, the donor and recipient are the same person.

The term "allogeneic" refers to cells or tissues that belong to or are obtained from the same species but that are genetically different, and which, in some cases, are therefore immunologically incompatible. Typically, the term "allogeneic" is used to define cells that are transplanted from a donor to a recipient of the same species.

The term "expression" refers to the process by which a polynucleotide is transcribed from a DNA template (such as into an mRNA or other RNA transcript) and/or the process by which a transcribed mRNA is subsequently translated into peptide, polypeptides or proteins. Transcripts and encoded polypeptides may be collectively referred to as "gene product." If the polynucleotide is derived from genomic DNA, expression may include splicing of the mRNA in a eukaryotic cell.

The term "heterologous" with reference to a protein or nucleic acid refers to a protein or nucleic acid originating from a different genetic source. For example, a protein or nucleic acid that is heterologous to a cell originates from an organism or individual other than the cell in which it is expressed.

As used herein, the term "introducing" encompasses a variety of methods of introducing DNA into a cell, either in vitro or in vivo, such methods including transformation, transduction, transfection (e.g. electroporation), and infection. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors.

The term "composition" refers to any mixture of two or more products, substances, or compounds, including cells or antibodies. It may be a solution, a suspension, liquid, powder, a paste, aqueous, non-aqueous or any combination thereof. The preparation is generally in such form as to permit the biological activity of the active ingredient (e.g. antibody) to be effective.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a kit is a packaged combination that optionally includes other elements, such as additional agents and instructions for use of the combination or elements thereof, for a purpose including, but not limited to, therapeutic uses.

As used herein, the term "treatment" or "treating" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disorder (e.g., an eosinophil-mediated disease) are mitigated or eliminated. For example, an individual is successfully "treated" if treatment results in increasing the quality of life of those suffering from a disease, decreasing the dose of other medications required for treating the disease, reducing the frequency of recurrence of the disease, lessening severity of the disease, delaying the development or progression of the disease, and/or prolonging survival of individuals.

An "effective amount" refers to at least an amount effective, at dosages and for periods of time necessary, to achieve the desired or indicated effect, including a therapeutic or prophylactic result. An effective amount can be provided in one or more administrations. A "therapeutically effective amount" is at least the minimum dose of cells required to effect a measurable improvement of a particular disorder. A therapeutically effective amount herein may vary according to factors such as the disease state, age, sex, and weight of the patient. A therapeutically effective amount may also be one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in subjects prior to or at the earlier stage of disease, the prophylactically effective amount can be less than the therapeutically effective amount.

As used herein, an "individual" or a "subject" is a mammal. A "mammal" for purposes of treatment includes humans, domestic and farm animals, and zoo, sports, or pet animals, such as dogs, horses, rabbits, cattle, pigs, hamsters, gerbils, mice, ferrets, rats, cats, etc. In some embodiments, the individual or subject is human.

II. Engineered NK Cells

Provided herein is an engineered NK cell that is genetically engineered to reduce FcRγ chain expression, activity and/or signaling in the cell. Also provided are methods for engineering the cells. In some embodiments, the methods include introducing a genetic disruption or inhibitory nucleic acid that disrupts a gene or represses expression of a gene resulting in reduced expression, activity and/or signaling of FcRγ chain in the NK cell.

In some embodiments, the engineered NK cell is genetically engineered to directly reduce or eliminate expression or activity of FcRγ chain. In some embodiments, the engineered NK cell is genetically engineered to indirectly reduce or eliminate expression or activity of FcRγ chain, such as by reducing or eliminating expression of a protein that regulates expression or activity of FcRγ, for example a transcription factor that controls expression of FcRγ. In some embodiments, the engineered NK cell is genetically engineered to reduce or eliminate expression or activity of a molecule involved in the downstream signaling of FcRγ. In some aspects, the engineered cell retains or is additionally engineered to transduce signals through CD3ζ, such as upon engagement or crosslinking of CD16.

Targets for Engineering

In some embodiments the NK cell is genetically engineered to reduce or eliminate expression or activity of human FcRγ chain protein. In some embodiments, the engineered NK cell comprises a genetic disruption of a gene encoding FcRγ chain or of a gene encoding a protein that regulates expression or activity of FcRγ chain protein. In some embodiments, the genetic disruption results in an insertion, deletion or mutation in the gene, such as a frameshift mutations and/or premature stop codons within the open reading frame. In some embodiments, one allele is disrupted. In some embodiments, both alleles are disrupted. In some embodiments the engineered NK cell comprises an inhibitory nucleic acid, such as an siRNA or other inhibitory nucleic acid molecule, that reduces expression of a gene encoding FcRγ chain or of a gene encoding a protein that regulates expression or activity of FcRγ chain protein.

An amino acid sequence for FcRγ chain (Homo sapiens, also called the High affinity immunoglobulin gamma Fc receptor I) is available in the NCBI database as accession number NP_004097.1 (GI:4758344), and is reproduced below as SEQ ID NO:1.

```
1    MIPAVVLLLL LLVEQAAALG EPQLCYILDA ILFLYGPVLT
41   LLYCRLKIQV RKAAITSYEK SDGVYTGLST RNQETYETLK
81   HEKPPQ
```

The NCBI database genomic reference sequence for FcRγ chain is NG_029043.1 RefSeqGene. The mRNA reference sequence is 1.NM_004106.1.

The engineered N K cell may contain a mutation, disruption, or deletion in the gene encoding FcRγ signaling adaptor, for example an inactivating mutation in an exon of the FcRγ chain gene. The mutation, disruption, or deletion can also be in a regulatory element of the FcRγ chain gene, for example, in the promoter.

Various inactivating mutations or deletions can also be used to decrease expression of FcRγ chain. For example, a mutation in the immunoreceptor tyrosine-based activation motif (ITAM) may be used. In some embodiments, the engineered NK cells may comprise an inactivating mutation in the ITAM motif. In other embodiments, the transmembrane region of FcRγ chain may be mutated to inactivate the protein.

In some embodiments, it is also possible to decrease FcRγ chain expression or activity, indirectly by increasing or decreasing expression of a protein that regulates FcRγ chain. In some embodiments, the engineered NK cell is genetically engineered to reduce or eliminate expression of a protein that regulates expression or activity of FcRγ chain, such as a transcription factor, e.g. PLZF or HELIOS. In some embodiments, the engineered NK cell comprises a genetic disruption of a gene encoding a protein that regulates expression or activity of FcRγ chain protein. In some embodiments, the genetic disruption results in an insertion, deletion or mutation in the gene, such as a frameshift mutations and/or premature stop codons within the open reading frame. In some embodiments, one allele is disrupted. In some embodiments, both alleles are disrupted. In some embodiments the engineered NK cell comprises an inhibitory nucleic acid that reduces expression of a gene encoding a protein that regulates expression or activity of FcRγ chain protein, such as a transcription factor, e.g. PLZF or HELIOS.

In some embodiments, the engineered NK cell may contain a genetic disruption, deletion, or mutation in a gene that promotes transcription of FcRγ signaling adaptor. In some embodiments, the engineered NK cell may have a genetic disruption, mutation, or deletion in a gene encoding a transcription factor that promotes transcription of the FcRγ chain. For example, the engineered NK cell may have a genetic disruption, in a gene encoding the PLZF or HELIOS transcription factor. In some embodiments, one allele of PLZF and/or HELIOS is disrupted. In some embodiments, both alleles of PLZF or both alleles of HELIOS are disrupted. In some embodiments, the engineered NK cell contains an inhibitory nucleic acid molecule, such as an siRNA or other inhibitory nucleic acid molecule, that reduces expression of a gene that promotes transcription of FcRγ signaling adaptor. In some embodiments, the engineered NK cell may have an inhibitory nucleic acid molecule that targets a transcription factor that promotes transcription of the FcRγ chain, such as an inhibitory nucleic acid molecule that targets a gene encoding the PLZF or HELIOS transcription factor.

The amino acid sequence of PLZF is available in the NCBI database as accession number NP_001018011.1, and is reproduced below as SEQ ID NO:3. The NCBI database genomic reference sequence is NG_012140.1. The mRNA reference sequence is NM_001018011.1.

```
MDLTKMGMIQLQNPSHPTGLLCKANQMRLAGTLCDVVIMVDSQEFHA
HRTVLACTSKMFEILFHRNSQHYTLDFLSPKTFQQILEYAYTATLQAKA
EDLDDLLYAAEILEIEYLEEQCLKMLETIQASDDNDTEATMADGGAEE
EEDRKARYLKNIFISHSSEESGYASVAGQSLPGPMVDQSPSVSTSFGLS
AMSPTKAAVDSLMTIGQSLLQGTLQPPAGPEEPTLAGGGRHPGVAEVK
TEMMQVDEVPSQDSPGAAESSISGGMGDKVEERGKEGPGTPTRSSVITS
ARELHYGREESAEQVPPPAEAGQAPTGRPEHPAPPPEKHLGIYSVLPNH
KADAVLSMPSSVTSGLHVQPALAVSMDFSTYGGLLPQGFIQRELFSKL
GELAVGMKSESRTIGEQCSVCGVELPDNEAVEQHRKLHSGMKTYGCE
LCGKRFLDSLRLRMHLLAHSAGAKAFVCDQCGAQFSKEDALETHERQT
HTGTDMAVFCLLCGKRFQAQSALQQHMEVHAGVRSYICSECNRTFPS
HTALKRHLRSHTGDHPYECEFCGSCFRDESTLKSHKRIHTGEKPYECNG
CGKKFSLKHQLETHYRVHTGEKPFECKLCHQRSRDYSAMIKHLRTHN
GASPYQCTICTEYCPSLSSMQKHMKGHKPEEIPPDWRIEKTYLYLCYV
```

The amino acid sequence of HELIOS (IKZF2) is available in the NCBI database as accession number NP_057344.2 (isoform 1) and NP_001072994.1 (isoform 2) The NCBI gene identifier is NC_000002.12. The mRNA reference sequence is NM_016260.2 (isoform 1) NM_001079526.1 (isoform 2). The gene ID is 22807.

In some embodiments, the engineered NK cell is genetically engineered to reduce or eliminate a protein involved in FcRγ chain-dependent signaling. In some embodiments, the engineered NK cell comprises a reduction in FcRγ chain-dependent signaling. For example, the engineered NK cell may have reduced expression of downstream molecules that is involved in FcRγ chain-dependent signaling. For example, Lee and Schlums describe members of the FcRγ signaling pathway that can be suitable targets for modification and/or deletion (Lee et al., Immunity 42:431-42 (2015); Schlums et al. Immunity, 42:443-56 (2015)). In some of these embodiments, the downstream molecules comprise SYK. DAB2 or EAT2. The gene ID for SYK is 6850. The NCBI gene ID for DAB2 is 1601. The genomic reference sequence for DAB2 is NG_030312.1. The mRNA and protein sequences for isoform 2 of DAB2 are 001244871.1 and NP_001231800.1. The mRNA and protein sequences for isoform 1 of DAB2 are 2.NM_001343.3 and NP_001334.2. The NCBI gene ID for EAT2 is 175072.

In some embodiments, the engineered NK cell may contain a have a genetic disruption, mutation, or deletion in a gene encoding a protein involved in FcRγ chain-dependent signaling. For example, the engineered NK cell may have a genetic disruption, in a gene encoding the SYK, DAB2 and/or EAT2. In some embodiments, one allele of SYK. DAB2 and/or EAT2 is disrupted. In some embodiments, both alleles of SYK, both alleles of DAB2 and/or both alleles of EAT2 are disrupted. In some embodiments, the engineered NK cell contains an inhibitory nucleic acid molecule, such as an siRNA or other inhibitory nucleic acid molecule, that reduces expression of a gene that is involved in FcRγ chain-dependent signaling. In some embodiments, the engineered NK cell may have an inhibitory nucleic acid molecule that targets a signaling molecule, such as an inhibitory nucleic acid molecule that targets a gene encoding SYK, DAB2 and/or EAT2.

Also provided are engineered NK cells that are genetically engineered to reduce or eliminate expression of an NK inhibitory receptor. In some aspects, any of the provided engineered that are engineered to have decreased expression, signaling, and/or activity of FcRγ chain as described above additionally can be engineered to reduce or eliminate expression of an NK inhibitory receptor. In some cases, the engineered cell contains a disruption of a gene encoding the NK inhibitory receptor. In some embodiments, the engineered cell contains an inhibitory nucleic acid molecule, such as an siRNA or other inhibitory nucleic acid molecule, that reduces expression of a gene encoding the NK inhibitory receptor. Inhibitory NK receptors are known in the art and include NKG2A (also known as KLRC1; NCBI gene ID 3821) and KIR2DL1 (NCBI gene ID 3802). The NK cell may be engineered to decrease expression of the inhibitory NK receptor using any of the methods provided herein, for example using an interfering RNA or genetic disruption, including a gene insertion, mutation, or deletion that produces a stop codon or frameshift.

In the above embodiments, such engineered NK cells include those that comprise genetic disruptions produced by nucleotide substitutions, deletions or additions. The substitutions, deletions or additions may involve one or more nucleotides. The variants may be altered in coding regions, non-coding regions, or both. Alterations in the coding regions may produce non-conservative amino acid substitutions, deletions or additions. In some embodiments, the genetic disruption comprises an insertion, deletion, or mutation that results in a premature stop codon in the gene or a frameshift of the open reading frame of the gene.

In some embodiments, the expression of a particular gene product, such as any described above, in the engineered cell is reduced by greater than about 10%, 20%, 30%, 40%, 50%, 60%, 70%, 75%, 80%, 85%, 90%, 95%, 98% or 99% as compared to the expression of the gene product in the NK cell that is not genetically engineered. In some embodiments, the expression of a particular gene product in the engineered cell is reduced to a level that is undetectable. In some embodiments, the expression of a particular gene product in the engineered cell is completely eliminated. In some of these embodiments, the gene is FcRγ chain. In other embodiments, the gene may encode a protein that regulates FcRγ chain, such as a transcription factor that promotes expression of FcRγ chain, such as PLZF or HELIOS. In other embodiments, the gene may encode a protein that is involved in FcRγ chain-mediated signaling, such as a such as downstream signaling molecules SYK, DAB2 or EAT2.

In some embodiments, the expression, activity and/or signaling of FcRγ chain in the provided engineered NK cells is reduced by greater than 10%, 20%, 30%, 40%, 50%, 60%, 70%, 75%, 80%, 85%, 90%, 95%, 98% or 99% as compared to the expression of the gene in the NK cell that is not genetically engineered. In some of these embodiments, the level of FcRγ chain expression is reduced to an undetectable level using an immunoblot assay.

In some embodiments, the engineered NK cell may express CD16 (also referred to as CD16A or FcγRIIIa). Thus, reference to CD16 herein is not meant to refer to the glycosylphosphatidylinositol-anchored form (FcγRIIIB or CD16B). In some of these embodiments, the CD16 is human CD16. In humans or as a glycosylphosphatidylinositol-anchored form (FcγRIIIB or CD16B). Typically, the provided engineered cells express a polypeptide-anchored CD16 form that is able to associated with the ζ chain of the TCR-CD3 complex. CD16 binds to antibody Fc regions and initiates ADCC. In some embodiments, the expression of other Fe receptor proteins is maintained in the engineered NK cell.

The genomic sequence for CD16A is available in the NCBI database at NG_009066.1. The gene ID for CD16A is 2214. Sequence information for CD16, including gene polymorphisms, is available at UniProt Ace. No. P08637. Nucleic acid and protein sequences for CD16a are publicly available. For example, GenBank Accession Nos. NM_000569 (SEQ ID NO: 1), NM_001127596. NM_001127595, NM_001127593, and NM_001127592 disclose exemplary human CD16a nucleic acid sequences, and GenBank Accession Nos. NP_000560 (SEQ ID NO: 2), NP_001121068, NP_001121067, NP_00112065, and NP_001121064 disclose exemplary human CD16a protein sequences. One of ordinary skill in the art can identify additional CD16a nucleic acid and amino acid sequences that vary from those provided herein, but that retain at least one activity of CD16a, such as Fc binding activity.

CD16 is most commonly found in a form that has a relatively low binding affinity for the Fc portion of IgG molecules. An alternative form that exhibits a higher binding affinity is found in some individuals. The low and high affinity forms of CD16 differ only by the substitution of valine (high affinity) for phenylalanine (low affinity) at position 158 in the mature (processed) form of the polypeptide chain. The sequence of CD16 (158F) is set forth in SEQ ID NO:4 (residue 158F is bold and underlined). In some embodiments, CD16 (158F) further comprises a signal peptide set forth as MWQLLLPTALLLLVSA (SEQ ID NO:5).

(SEQ ID NO: 4)
GMRTEDLPKAVVFLEPQWYRVLEKDSVTLKCQGAYSPEDNSTQWFHNESL

ISSQASSYFIDAATVDDSGEYRCQTNLSTLSDPVQLEVHIGWLLLQAPRW

VFKEEDPIHLRCHSWKNTALHKVTYLQNGKGRKYFHHNSDFYIPKATLKD

-continued
SGSYFCRGLFGSKNVSSETVNITITQGLAVSTISSFFPPGYQVSFCLVMV

LLFAVDTGLYFSVKTNIRSSTRDWKDHKFKWRKDPQDK

The sequence of CD16 158V (polymorphism resulting in F158V) is known as VAR_003960 and has the sequence set forth in SEQ ID NO:6 (158V polymorphism is in bold and underline). In some embodiments, CD16 (158V) further comprises a signal peptide set forth as MWQLLLP-TALLLLVSA (SEQ ID NO:5).

(SEQ ID NO: 6)
GMRTEDLPKAVVFLEPQWYRVLEKDSVTLKCQGAYSPEDNSTQWFHNESL

ISSQASSYFIDAATVDDSGEYRCQTNLSTLSDPVQLEVHIGWLLLQAPRW

VFKEEDPIHLRCHSWKNTALHKVTYLQNGKGRKYFHHNSDFYIPKATLKD

SGSYFCRGLVGSKNVSSETVNITITQGLAVSTISSFFPPGYQVSFCLVMV

LLFAVDTGLYFSVKTNIRSSTRDWKDHKFKWRKDPQDK

In some embodiments, the engineered NK cell may comprise a CD16 gene that comprises an activating mutation. In some of embodiments, the mutation results in higher affinity to an IgG region. In some of these embodiments, the CD16 mutation results in higher affinity of CD16 for IgG1, IgG2, or IgG4. In some embodiments, the CD16 mutation results in higher affinity of CD16 for IgG1. In some embodiments, the CD16 contains the 158V mutation. In some embodiments, the CD16 has the sequence of amino acids set forth in SEQ ID NO:6 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:6 and that contains the 158V polymorphism. In some embodiments, the mutation in CD16 is a 158F mutation. In some embodiments, the CD16 has the sequence of amino acids set forth in SEQ ID NO:4 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:4 and that contains the 158F polymorphism.

In some aspects, the engineered NK cells can be engineered to express a recombinant or heterologous CD16. In some embodiments, even if the NK cells may express CD16, the NK cells may be engineered to further express a higher level of CD16 and/or express a modified form of CD16 than is expressed by the NK in the absence of the genetic engineering. In such examples, the cells can be engineered to contain nucleic acid comprising a strong or constitutive promotor followed by a CD16 gene.

The engineered NK cell may also express other signaling adaptor molecules. For example, signaling molecules with an ITAM domain other than FcRγ. In some embodiments, the engineered NK cell expresses CD3ζ adaptor chain. In some of these embodiments, CD3ζ is human CD3ζ.

An amino acid sequence for the human CD3ζ (*Homo sapiens*) is available in the NCBI database as accession number ABQ28690.1 (GI: 146399947), and is reproduced below as SEQ ID NO:2.

```
 1    AILQAQLPIT EAQSFGLLDP KLCYLLDGIL FIYGVILTAL
41    FLRVKFSRSA DAPAYQQGQN QLYNELNLGR REEYDVLDKR
81    RG
```

The NCBI gene ID for CD3ζ (CD247) is 919.

In some aspects, the engineered NK cells can be engineered to express a recombinant or heterologous CD3ζ. In some embodiments, even if the NK cells may express CD3ζ, the NK cells may be engineered to further express a higher level of CD3ζ and/or express a modified form of CD3ζ than is expressed by the NK in the absence of the genetic engineering. In such examples, the cells can be engineered to contain nucleic acid comprising a strong or constitutive promotor followed by a CD3ζ gene. In some embodiments, the engineered cells may comprise a CD3ζ gene with an activating mutation. In other embodiments, the engineered NK cells may express CD3ζ at a higher level after engineering.

In some embodiments, the engineered NK cell may have reduced expression of NK cell surface receptors, including natural cytotoxicity receptors. The engineered NK cell may have reduced expression of NKp46, NKp30, and/or NKp44 compared to the NK cell without the modification. In some of these embodiments, the expression of the cell surface receptor is reduced by greater than 1.2 fold, 1.5 fold, 2 fold, 3 fold, 4 fold, 10 fold, 100 fold or 1000 fold. In some of these embodiments the NK cell surface receptor may not be detectable in the engineered NK cell. In other embodiments, the NK cell may be negative for NK cell surface receptors, such as NKp46, NKp30, and/or NKp44.

Cell Types

One of skill in the art will appreciate that both primary cells obtained from human tissue and existing cell lines are suitable for engineering. For example, in some embodiments, the engineered NK cell may be derived from a primary cell obtained from a subject, such as a human.

Primary Cells

Primary cells can be engineered using any of the methods provided herein. According to some embodiments the population of cells comprising said NK cells is obtained from a sample from a mammalian subject, such as a human subject. The sample or source can be cord blood, bone marrow or peripheral blood.

In some aspects, Natural killer cells expressing one or more natural killer cell-specific markers are isolated from the cell population. Methods of isolating and identifying NK cells are well known in the art, and include those discussed in Dahlberg et al, Frontiers in Immunology, vol. 6 article 605 pp. 1-18 (2015).

Techniques for the in vitro isolation and large-scale expansion of NK cells are known. An exemplary procedure is described in US Pat. App. Publ. No. 2014/0086890, incorporated herein by reference in its entirety. One of ordinary skill in the art can identify additional methods for expanding NK cells, for example as described in Childs et al., Hematol. The Education Program 2013:234-246, 2013, incorporated herein by reference in its entirety.

In some embodiments, mononuclear cells are collected from a subject (such as a donor subject or a subject with a tumor or hyperproliferative disease). In some examples, mononuclear cells are collected by an apheresis procedure. The mononuclear cells are enriched for NK cells, for example by negative depletion using an immuno-magnetic bead strategy. In some examples, NK cells are enriched by depleting the mononuclear cell sample of T cells, B cells, monocytes, dendritic cells, platelets, macrophages, and erythrocytes utilizing a mixture of biotinylated monoclonal antibodies. The non-NK cells in the sample are removed with magnetic beads coupled to streptavidin, resulting in an enriched preparation of NK cells. An exemplary commercially available kit for this method is Dynabeads®

Untouched™ Human NK Cells kit (Thermo Fisher Scientific, Waltham, MA). In another example, NK cells are enriched by positive selection of CD56' NK cells, for example utilizing magnetic beads conjugated to an anti-CD56 antibody (such as CD56 MicroBeads, Miltenyi Biotec, Inc., Auburn, CA). In other examples, a two-step method including negative depletion (such as T cell depletion) followed by positive selection of CD56$^+$ NK cells is used for enriching NK cells.

In some embodiments, Natural killer cells may be identified as those expressing typical human natural killer cell markers such as KIR, NKG2A, NKG2D, NKp30, NKp44, NKp46, CD56, and CD161. For studies involving mice, natural killer cells can be identified and/or isolated using typical mouse markers such as NK1.1, CD 122, LY49 Family (Ly49A, Ly49C, Ly49D, Ly49E, Ly49F, Ly49G, Ly49H, and Ly49I), or NKG2A/C/E. In some embodiments, cell staining, or FACS may be used to identify cells that express a certain marker.

In some embodiments, NK cells can be selectively enriched using either positive or negative selection. For example, NK cells that do not express CD3 can be selected by exposing a mixture of cells to an immobilized anti-CD3 antibody and removing the unbound cells. According to some embodiments of the present invention the NK cells comprise CD56+CD3− cells. According to some embodiments of the present invention the NK cells comprise CD56+CD16+CD3− cells.

In one embodiment, cytokines can be administered to a subject prior to isolating primary NK cells. For example, IL-12, IL-15, IL-18, IL-2, and/or CCL5 can be administered to a subject prior to isolating the primary NK cells.

It may also be beneficial to enrich the isolated NK primary cells for those that express CD16 and CD3ζ. One of skill in the art will appreciate that many methods exist for selectively enriching cells expressing certain markers from population exist, such as fluorescent cell sorting, or selective depletion of cells expressing certain markers using antibodies bound to a solid phase.

In some embodiments, the methods can be carried out under or adapted for Current Good Manufacturing Practice (cGMP). One of ordinary skill in the art can identify other methods that can be used to prepare an enriched population of NK cells.

In some embodiments, enriched NK cells (typically >99% CD3 negative and >85% CD56+) are expanded in vitro prior to or after genetically engineering the cells.

In one non-limiting example, the enriched NK cells are cultured with an irradiated EBV-LCL feeder cell line (SMI-LCL) in X-VIVO™ 20 medium (Lonza, Basel, Switzerland) with 10% human AB serum and 500 IU/ml of interleukin-2 (IL-2), for up to 21 days. Utilizing this technique, expansions of NK cells in the range of 200- to 1000-fold may be achieved (expanded NK cells are typically >99% CD3 negative and >90% CD56+). In some examples, the starting population of enriched NK cells is about 0.8-1.6×10$^8$ total NK cells, which over a 2-4 week period expand up to 1000-fold or greater in vitro. Similar numbers of NK cells have been expanded in scaled up experiments using GMP conditions. In some examples, NK cells are expanded in G-Rex® containers (Wilson Wolf, New Brighton, MN). The G-Rex®100 container support NK expansions to doses of 2.5×10$^8$ NK cells/kg or higher. NK cells cultured in G-Rex®100 containers could be cultured at concentrations up to 4×10$^6$ NK cells/ml.

In some embodiments, bulk NK cells or NK cells subsets isolated by additional enriching procedures, such as through the use of immune-magnetic beads or flow sorting, may be grown in cell culture medium, e.g., Cellgro SCGM serum-free media (CellGenix, Gaithersburg, MD) containing 10% human AB serum, 50 U/mL penicillin, 50 gig/mL streptomycin, and 500 IU/mL IL-2 or in X-VIVO™ 20 media containing 10% heat inactivated human AB serum or 10% autologous serum.

Non-expanded and expanded NK cells can be analyzed by flow cytometry for the expression of markers such as CD56, CD16, TRAIL, FasL, NKG2D, LFA-1, perforin, and granzymes A and B. In some examples, expression of one or more of the markers is measured at baseline and >10 days following in vitro expansion. Chromium release assays can be used to assess fresh vs. expanded NK cell cytotoxicity against cancer cell targets. One of ordinary skill in the art can identify other methods to assess the NK cell population (for example, purity), viability, and/or activity.

In some embodiments, expand primary cells derived from a subject may be expanded and/or cultured before genetic engineering. In some embodiments the engineered primary cells are cultured and/or expanded following engineering and prior to administration to a patient.

NK Cell Line

In some embodiments, NK cell lines can be engineered as described herein. In some embodiments, the engineering NK cells include engineered NK cell lines. In some aspects, engineered cell lines allow production of higher amounts of cells without having to expand small numbers of NK cells that are derived from a subject. Engineered cell lines also have the advantage of being well characterized.

In some embodiments, the cell line is a clonal cell line. In some embodiments, the cell line is derived from a patient with NK-cell leukemia or lymphoma. In some embodiments, the NK cell line comprises NK-92, NK-YS, KHYG-1, NKL, NKG, SNK-6, or IMC-1.

The NK-92 is a NK-like cell line that was initially isolated from the blood of a subject suffering from a large granular lymphoma and subsequently propagated in cell culture. The NK-92 cell line has been described (Gong et al., 1994; Klingemann, 2002). NK-92 cells have a CD3−/CD56+ phenotype that is characteristic of NK cells. They express all of the known NK cell-activating receptors except CD16, but lack all of the known NK cell inhibitory receptors except NKG2A/CD94 and ILT2/LIR1, which are expressed at low levels. Furthermore, NK-92 is a clonal cell line that, unlike the polyclonal NK cells isolated from blood, expresses these receptors in a consistent manner with respect to both type and cell surface concentration. Similarly, NK-92 cells are not immunogenic and do not elicit an immune rejection response when administered therapeutically to a human subject. Indeed NK-92 cells are well tolerated in humans with no known detrimental effects on normal tissues.

Some existing cell lines, such as NK-92 do not naturally express CD16. In some embodiments, the method provided herein includes engineering a NK cell line, such as NK-92, to express CD16. Klingemann et al., also discuss the advantages of the NK92 cell lines. Klingemann et al, Frontiers in Immunology, vol 7, article 91 pp 1-7 (2016) In some embodiments, the methods provided herein include engineering a cell line to express CD3ζ. In some embodiments CD16 and/or CD3ζ can be expressed inducibly or transiently. In such embodiments, the cell line is not engineered to heterologously or recombinantly express FcRγ chain or is engineered to reduce or eliminate expression of FcRγ chain in the cell.

Methods of Producing Engineered NK Cells

Provided herein are methods of producing an engineered NK cell that is genetically engineered to reduce FcRγ chain expression, activity and/or signaling in the cell as described. For example, the method may comprise introducing a genetic disruption of a gene encoding FcRγ chain, a gene encoding a protein that regulates expression or activity of FcRγ signaling adaptor (e.g. a transcription factor, such as PLZF or HELIOS) and/or a gene encoding a protein that is involved in FcRγ-mediated signaling (e.g. a downstream signaling molecule, such as SYK, DAP2 or EAT2) as described. In some embodiments, the method may comprise introducing an inhibitory nucleic acid molecule that targets a gene encoding FcRγ chain, a gene encoding a protein that regulates expression or activity of FcRγ signaling adaptor (e.g. a transcription factor, such as PLZF or HELIOS) and/or a gene encoding a protein that is involved in FcRγ-mediated signaling (e.g. a downstream signaling molecule, such as SYK, DAP2 or EAT2) as described.

In some embodiments, the method provided herein comprises isolating an NK cell from a subject, such as by the methods as described above or known to a skilled artisan, and reducing the expression of FcRγ chain expression, activity and/or signaling in the cell in accord with the provided methods. In some embodiments, the method provided herein comprises obtaining an NK cell line, such as any described herein, and engineering the cell to reduce expression of FcRγ expression, activity and/or signaling in the cell in accord with the provided methods.

One of ordinary skill in the art will appreciate that there are many ways of decreasing the expression or activity of FcRγ. For example, the level of transcription can be decreased. One method of decreasing gene expression, such as FcRγ chain expression, involves modifying an endogenous gene to decrease transcription. For example, the FcRγ chain gene may be deleted, disrupted, or mutated. In addition to targeting the FcRγ RNA, mutating, or modifying the FcRγ gene, FcRγ protein level can be decreased by effecting a molecule that increases FcRγ gene expression or activity, such as a transcription factor that regulates transcription of FcRγ. In some embodiments a gene that regulates transcription or translation of the FcRγ chain gene may be deleted, disrupted, or mutated. In some of these embodiments, the gene is a transcription factor that regulates expression of the FcRγ chain gene. Specifically, inhibition of a transcription factor that positively regulates FcRγ expression will result in decreased FcRγ expression. Transcription factors that regulate FcRγ transcription include HELIOS and PLZF.

One of ordinary skill in the art will understand that there are many suitable methods for disrupting FcRγ chain gene or other gene, such as those described herein. For example, the entire gene locus, such as FcRγ locus, may be deleted. In some cases, it is also suitable to delete a portion of the gene, for example an exon, or a domain. Specifically, the ITAM signaling domain of FcRγ may be deleted. Alternatively, the provided methods also include introducing one or more amino acid substitutions into the gene locus, such as FcRγ locus, such as an inactivating mutation. In some embodiments, a stop codon can be introduced into the mRNA, such as FcRγ mRNA, to produce a truncated and/or inactivated form of the expressed gene, such as FcRγ signaling adaptor. In some embodiments, regulatory elements of the gene, such as FcRγ gene, can also be mutated or deleted in order to reduce expression, activity and/or signaling of FcRγ signaling adaptor.

In some embodiments, gene disruption can be carried out in mammalian cells using site-specific endonucleases. Endonucleases that allow for site-specific deletion of a gene are well known in the art and may include TAL nucleases, meganucleases, zinc-finger nucleases, Cas9, and Argonaute. Methods for producing engineered, site-specific endonucleases are known in the art. The site-specific endonuclease can be engineered to recognize and delete or modify a specific gene, such as the FcRγ chain gene.

In one embodiment, zinc-finger nucleases (ZFNs) can be engineered to recognize and cut predetermined sites in a genome. ZFNs are chimeric proteins comprising a zinc finger DNA-binding domain fused to the nuclease domain of the FokI restriction enzyme. The zinc finger domain can be redesigned through rational or experimental means to produce a protein which binds to a pre-determined DNA sequence, about or approximately 18 basepairs in length. By fusing this engineered protein domain to the FokI nuclease, it is possible to target DNA breaks with genome-level specificity. ZFNs have been used extensively to target gene addition, removal, and substitution in a wide range of eukaryotic organisms (reviewed in S. Durai et al., Nucleic Acids Res 33, 5978 (2005)).

In other embodiments, TAL-effector nucleases (TALENs) can be generated to cleave specific sites in genomic DNA. Like a ZFN, a TALEN comprises an engineered, site-specific DNA-binding domain fused to the FokI nuclease domain (reviewed in Mak, et al. (2013) Curr Opin Struct Biol. 23:93-9). In this case, however, the DNA binding domain comprises a tandem array of TAL-effector domains, each of which specifically recognizes a single DNA basepair. Because ZFNs and TALENs are heterodimeric so that the production of a single functional nuclease in a cell requires co-expression of two protein monomers, compact TALENs provide an alternative endonuclease architecture that avoids the need for dimerization (Beurdeley, et al. (2013) Nat Commun. 4: 1762). A Compact TALEN comprises an engineered, site-specific TAL-effector DNA-binding domain fused to the nuclease domain from the I-TevI homing endonuclease. Unlike FokI, I-TevI does not need to dimerize to produce a double-strand DNA break so a Compact TALEN is functional as a monomer.

In some embodiments, engineered endonucleases based on the CRISPR/Cas9 system are also known in the art and can be employed in the provided methods to engineer the cells (Ran, et al. (2013) Nat Protoc. 8:2281-2308; *Mali* et al. (2013) Nat Methods. 10:957-63). A CRISPR endonuclease comprises two components: (1) a caspase effector nuclease, typically microbial Cas9; and (2) a short "guide RNA" that directs the nuclease to a location of interest in the genome. In some embodiments, the guide RNA comprises an approximately 20 nucleotide targeting sequence. By expressing multiple guide RNAs in the same cell, each having a different targeting sequence, it is possible to target DNA breaks simultaneously to multiple sites in in the genome. Methods of using CRISPR-Cas9 are well known in the art.

In some aspects, the guide sequence is any polynucleotide sequence comprising at least a sequence portion that has sufficient complementarity with a target polynucleotide sequence, such as a gene encoding FcRγ, PLZF, HELIOS, SYK, DAB2 or EAT2, to hybridize with the target sequence and direct sequence-specific binding of the CRISPR complex to the target sequence. Typically, in the context of formation of a CRISPR complex, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some embodiments, a guide sequence is selected to reduce the degree of secondary structure within the guide sequence. Secondary structure may be determined by any suitable polynucleotide folding algorithm.

In some embodiments, a CRISPR enzyme (e.g. Cas9 nuclease) in combination with (and optionally complexed with) a guide sequence is delivered to the cell. In some embodiments, one or more elements of a CRISPR system is derived from a type I, type II, or type III CRISPR system. In some embodiments, one or more elements of a CRISPR system are derived from a particular organism comprising an endogenous CRISPR system, such as *Streptococcus pyogenes* or *Staphylococcus aureus*.

In the one embodiment of the invention, the DNA break-inducing agent is an engineered homing endonuclease (also called a "meganuclease"). Homing endonucleases are a group of naturally-occurring nucleases which recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), Q. Rev. Biophys. 38: 49-95). Homing endonucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif (see Chevalier et al. (2001), Nucleic Acids Res. 29(18): 3757-3774). The LAGLIDADG homing endonucleases with a single copy of the LAGLIDADG motif form homodimers, whereas members with two copies of the LAGLIDADG motif are found as monomers.

Another method of decreasing FcRγ chain expression, activity and/or signaling involves introducing an inhibitory nucleic acid, such as an inhibitory RNA, into the cell that targets, e.g. is complementary to, a target gene transcript, such as an FcRγ, PLZF, HELIOS, SYK, DAB2 or EAT2 gene transcript, thereby reducing expression of the gene product. For example the nucleic acid may target FcRγ chain mRNA. In other embodiments, the inhibitory nucleic acid may target the mRNA of a gene that regulates transcription or translation of the FcRγ chain gene, such as a transcription factor, for example PLZF or HELIOS mRNA. In some embodiments the nucleic acid targets the mRNA of gene encoding a protein involved in FcRγ-mediated signaling, such as SYK, DAB2 or EAT-2 mRNA.

The presently disclosed subject matter takes advantage of RNAi technology (for example shRNA, siRNA and miRNA molecules and ribozymes) to cause the down regulation of cellular genes, a process referred to as RNA interference (RNAi). As used herein, "RNA interference" (RNAi) refers to a process of sequence-specific post-transcriptional gene silencing mediated by a small interfering RNA (siRNA) or short hairpin RNA (shRNA) molecules, miRNA molecules or synthetic hammerhead ribozymes. See generally Fire et al., Nature 391:806-811, 1998, and U.S. Pat. No. 6,506,559. The process of RNA interference (RNAi) mediated post-transcriptional gene silencing is thought to be an evolutionarily conserved cellular defense mechanism that has evolved to prevent the expression of foreign genes (Fire, Trends Genet 15:358-363, 1999).

In some embodiments, a recombinant virus comprising nucleic acid encoding the RNA can be produced. Engineering retroviral vectors is known to those having ordinary skill in the art. Such a skilled artisan would readily appreciate the multiple factors involved in selecting the appropriate virus and vector components needed to optimize recombinant virus production for use with the presently disclosed subject matter without the necessity of further detailed discussion herein. As one non-limiting example, a retrovirus can be engineered comprising DNA encoding an shRNA comprising an siRNA.

The gene expression may be reduced permanently, transiently, or inducibly. Suitable inducible systems are well known and include eukaryotic promoters responsive to heavy metals, Lac/VP16, and the tetracycline repressor system.

On the other hand, it may be beneficial to permanently reduce expression of the gene, for example by producing a cell line with a deletion, substitution, or insertion that causes inactivation of the gene.

Retroviral systems can be used to introduce cDNAs into NK cells. Methods of eukaryotic cell transfection and prokaryotic cell transformation are well known in the art. The choice of host cell dictates the preferred technique for introducing the polynucleotide of interest. Introduction of polynucleotides into an organism may also be done with ex vivo techniques that use an in vitro method of transfection, as well as established genetic techniques, if any, for that particular organism.

Other vectors and packaging cell lines have been used in the preparation of genetically modified variants of NK cells and can be used equivalently herein. Retroviral transduction systems have also been successfully used to transduce a variety of genes into NK cells. By way of example, these alternative methods include, but are not limited to the p-JET vector in conjunction with FLYA13 packaging cells (Gerstmayer et al., 1999), the plasmid-based kat retroviral transduction system, and DFG-hIL-2-neo/CRIP (Nagashima et al., 1998). Electroporation and "gene gun" introduction of the vector into the packaging cells is also practiced. Use of the pBMN-IRES-EGFP vector in combination with the Phoenix-Amphotropic packaging cell line is convenient for the purpose of this and the following Examples in that it provides high efficiencies of Phoenix-Amphotropic cell transfection; the use of Moloney LTR promoters results in a high level of CD16 expression; the virus is produced at high titers; the efficiency of NK transduction is improved over other vectors that have been used to transduce NK cells; and the vector provides adequate space to accommodate the CD16 cDNA or alternative inserts. The pBMN-IRES-EGFP vector further incorporates genes for enhanced green fluorescent protein (EGFP), which can be used as an endogenous surrogate marker for gene expression. The Phoenix cell line stably expresses this vector in episomal form along with producing other viral components, thus allowing the cells to stably produce virus for an extended period of time.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20 deg. C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules.

Regardless of the method used to introduce exogenous nucleic acids into a host cell or otherwise engineer the cell in accord with the provided methods, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR or "biochemical" assays, such as detecting the presence or absence of a particular peptide, e.g., by immunological means (ELISAs and Western blots).

Features of Engineered Cells

The expression of gene products associated with the engineering of genes as described can be assessed following or in connection with the engineering and/or culturing of the NK cells. Any available procedure known to a skilled artisan can be employed to detect the gene products so long as the procedure does not injure the cells. For example, the NK cells can be detected, identified and/or isolated by flow cytometry for detection of a cell surface marker that correlates with expression of the gene product, such as that correlates with FcRγ expression. The targets for modulating expression by genetic engineering as described, such as FcRγ proteins, are intracellular proteins that are not easily detected unless the cells are treated to allow intracellular proteins to be detected, for example, by fixation and permeabilization.

In some embodiments, the methods provided herein result in expression of a particular gene product in the engineered cell that is reduced by greater than about 10%, 20%, 30%, 40%, 50%, 60%, 70%, 75%, 80%, 85%, 90%, 95%, 98% or 99% as compared to the expression of the gene product in the NK cell that is not genetically engineered. In some embodiments, the methods provided herein reduce FcRγ chain expression by greater than 10%, 20%, 30%, 40%, 50%, 60%, 70%, 75%, 80%, 85%, 90%, 95%, 98% or 99% as compared to the expression of FcRγ chain in the NK cell that is not genetically engineered. In some of these embodiments, the level of FcRγ chain expression is reduced to an undetectable level using an immunoblot assay.

Expression of gene products as described, such as FcRγ chain expression, can be measured in a variety of ways. For example, RNA expression can be measured by northern blot, qPCR, and FISH. Protein expression can also be measured, for example using flow cytometry, western blot, immunohistochemistry, ELISA, and the like.

In some aspects, the provided engineered NK cells exhibit enhanced activity when activated by antibody, such as can occur by antibody-mediated crosslinking of CD16 or by antibody-coated cells, e.g. antibody-coated tumor cells. In some embodiments, the provided engineered NK cells are particular responsive in the presence of an antibody or other Fc-containing protein and can be used in methods in combination with an administered monoclonal antibody or other Fc-containing protein specific to a tumor, virus or microbial cell. In some cases, the provided engineered NK cells exhibit properties or features that are the same as or similar to g-NK cells, which are a specific subset of NK cells deficient in FcRγ present in small numbers in individuals, but only in about one-third of the population (see e.g. published patent appl. No. US2013/0295044; see also Hwang et al. (2012) Int. Immunol., 24:793-802 and Lee et al. (2015) Cell Immunity, 42:431-442)).

In some embodiments, the increased activity is observed following CD16 engagement by CD16 crosslinking, such as can occur in the presence of an antibody by binding of the Fc portion of the antibody to CD16 and initiation of ADCC. In some embodiments, the increased activity can be determined by monitoring phosphorylation of the CD3ζ chain, signaling molecules, CA2+ flux, expression or secretion of cytokines by the cell (e.g. IFN-gamma or TNF-α), expression or secretion of chemokines by the engineered cell (MIP-1α, MIP-1β or RANTES), degranulation response, expression of Granzyme B and/or cytotoxic killing response. Any of a number of well-known assays can be used to assess the properties or activities of the engineered NK cells (see e.g. Hwang et al. (2012) Int. Immunology, 24:793-802; published patent appl. No. US2013/0295044). In some embodiments, the activity of the engineered NK cells following CD16 crosslinking or engagement is increased by greater than or greater than about 1.2-fold, 1.5-fold, 2-fold, 3-fold, 4-fold, 5-fold, 6-fold, 7-fold, 8-fold, 9-fold, 10-fold or more compared to in the activity in the engineered NK cell in the same assay but in the absence of CD16 crosslinking or engagement.

In vitro assays are commonly employed for assessing antibody-dependent cellular cytotoxicity (ADCC). In one example, target cells (e.g. cells that express an antigen that is appropriate to the antibody being evaluated) are loaded with an indicator material (such as 51Cr), and the indicator-loaded target cells are treated with the antibody to be evaluated. The resulting cells are exposed to NK effector cells as described herein. Lysis of the target cells is indicated by the release of the indicator material into the assay supernatant where its concentration can be measured by a suitable method such as scintillation counting (51Cr) or fluorescence intensity or lifetime determination. Efficacy can likewise be assessed by the measurement of surrogate indicators such as cytokine release by the NK cells; the up-regulation of NK cell activation markers, such as CD25, CD69 and/or CD95L; activation of NK cell transcription factors, such as NF-AT or NF-κB; or the activation of caspases or other markers of apoptosis in the target cells. Parental NK cells (such as non-genetically engineered NK cells) serve as a control because they permit differentiating between ADCC-mediated cytotoxicity and other cytolytic effects that NK cells exert on the target cells.

In some embodiments, the engineered NK cells are able to persist in an individual for an extended period and therefore the number of times that the cells need to be administered to have a therapeutic effect can be decreased. In some embodiments, the engineered cells provided herein persist for at least one month, at least two months, at least three months, at least four months, at least five months, at least six months, or at least months after administration.

III. Compositions and Kits Comprising Engineered NK Cells

Provided herein are compositions comprising the provided engineered NK cells. Among the compositions are pharmaceutical compositions and formulations for administration, such as for adoptive cell therapy. In some embodiments, the engineered cells are formulated with a pharmaceutically acceptable carrier.

A pharmaceutically acceptable carrier can include all solvents, dispersion media, coatings, antibacterial and antifungal agents, isotonic and absorption delaying agents, and the like, compatible with pharmaceutical administration (Gennaro, 2000, Remington: The science and practice of pharmacy, Lippincott, Williams & Wilkins, Philadelphia, PA). Examples of such carriers or diluents include, but are not limited to, water, saline, Ringer's solutions, dextrose solution, and 5% human serum albumin. Liposomes and non-aqueous vehicles such as fixed oils may also be used. Supplementary active compounds can also be incorporated into the compositions. The pharmaceutical carrier should be one that is suitable for NK cells, such as a saline solution, a dextrose solution or a solution comprising human serum albumin.

In certain embodiments, the number of cells in the composition provides the engineered NK cells at a therapeutically effective amount. In some embodiments, the amount is an amount that reduces the severity, the duration and/or the symptoms associated with cancer, viral infection, microbial infection, or septic shock in an animal. In certain other embodiments, a therapeutically effective amount is a dose of cells that results in a reduction of the growth or spread of cancer by at least 2.5%, at least 5%, at least 10%, at least 15%, at least 25%, at least 35%, at least 45%, at least 50%, at least 75%, at least 85%, by at least 90%, at least 95%, or at least 99% in a patient or an animal administered a composition described herein relative to the growth or spread of cancer in a patient (or an animal) or a group of patients (or animals) not administered the composition. In some embodiments, an effective amount for cytotoxicity is defined as amount of engineered NK cells that is able to inhibit or reduce the growth of cancer, viral and microbial cells. In some embodiments, the composition comprises a dose of engineered NK cells that is from or from about $10^5$ to about $10^{12}$ cells, or about $10^5$ to about $10^8$ cells, or about $10^6$ to about $10^{12}$ cells, or about $10^8$ to about $10^1$ cells, or about $10^9$ to about $10^{10}$ cells. In some embodiments, the composition comprises greater than or greater than about $10^5$, about $10^6$, about $10^7$, about $10^8$, about $10^9$, about $10^{10}$, about $10^{11}$, or about $10^{12}$ cells.

In some embodiments, the volume of the composition is at least or at least about 10 mL, 50 mL, 100 mL, 200 mL, 300 mL, 400 mL or 500 mL, such as is from or from about 10 mL to 500 mL, 10 mL to 200 mL, 10 mL to 100 mL, 10 mL to 50 mL, 50 mL to 500 mL, 50 mL to 200 mL, 50 mL to 100 mL, 100 mL to 500 mL, 100 mL to 200 mL or 200 mL to 500 mL, each inclusive. In some embodiments, the composition has a cell density of at least or at least about $1\times10^5$ cells/mL, $5\times10^5$ cells/mL, $1\times10^6$ cells/mL, $5\times10^6$ cells/mL, $1\times10^7$ cells/mL, $5\times10^7$ cells/mL or $1\times10^8$ cells/mL. In some embodiment, the cell density of the composition is between or between about $1\times10^5$ cells/mL to $1\times10^8$ cells/mL, $1\times10^5$ cells/mL to $1\times10^7$ cells/mL, $1\times10^5$ cells/mL to $1\times10^6$ cells/mL, $1\times10^6$ cells/mL to $1\times10^7$ cells/mL, $1\times10^6$ cells/mL to $1\times10^8$ cells/mL, $1\times10^6$ cells/mL to $1\times10^7$ cells/mL or $1\times10^7$ cells/mL to $1\times10^8$ cells/mL, each inclusive.

Depending upon the method of engineering the NK cell, it may be necessary or desirable to culture the NK cells to expand them prior to formulating them as a composition for administration. In some of the embodiments, methods of producing a composition comprising engineered NK cells comprises culturing or incubating the engineered NK cells, such as to expand the cells to a therapeutically effective amount prior to administering the NK cells to an individual in need thereof.

Suitable methods for culturing and expanding NK cells are known. For example, the NK cells may be cultured using feeder cells, or in the presence of cytokines to enhance their growth and/or activation. As used herein "culturing" includes providing the chemical and physical conditions (e.g., temperature, gas) which are required for NK cell maintenance, and growth factors. In one embodiment, culturing the NK cells includes providing the NK cells with conditions for proliferation. Examples of chemical conditions which may support NK cell proliferation include but are not limited to buffers, nutrients, serum, vitamins and antibiotics as well as cytokines and other growth factors which are typically provided in the growth (i.e., culture) medium. In one embodiment, the NK culture medium includes MEMα comprising 10% FCS or CellGro SCGM (Cell Genix) comprising 5% Human Serum/LiforCell® FBS Replacement (Lifeblood Products). Other media suitable for use with the invention include, but are not limited to Glascow's medium (Gibco Carlsbad Calif.), RPMI medium (Sigma-Aldrich, St Louis Mo.) or DMEM (Sigma-Aldrich, St Louis Mo.). It will be noted that many of the culture media contain nicotinamide as a vitamin supplement for example, MEMα (8.19 µM nicotinamide), RPMI (8.19 µM nicotinamide), DMEM (32.78 µM nicotinamide) and Glascow's medium (16.39 µM nicotinamide).

In some embodiments, such as for applications in which cells are introduced (or reintroduced) into a human subject, culturing is carried out using serum-free formulations, such as AIM V™ serum free medium for lymphocyte culture or MARROWMAX™ bone marrow medium. Such medium formulations and supplements are available from commercial sources such as Invitrogen (GIBCO) (Carlsbad, Calif.). The cultures can be supplemented with amino acids, antibiotics, and/or with cytokines to promote optimal viability, proliferation, functionality and/or and survival.

In some embodiments, culturing the population of cells comprising the engineered NK cells is effected without a feeder layer or feeder cells. In some of these embodiments, the engineered NK cells can be cultured with a growth factor. According to some embodiments, the at least one growth factor comprises a growth factor selected from the group consisting of SCF, FLT3, IL-2, IL-7, IL-15, IL-12 and IL-21. According to some embodiments, the at least one growth factor is IL-2 or IL-2 and IL-15. According to some embodiments, the at least one growth factor is solely IL-2.

In some embodiments, the provided compositions include those in which the genetically engineered NK cells, such as engineered NK cells that are reduced for FcRγ chain expression, activity and/or signaling in the cell, make up at least or at least about 60%, 70%, 80%, 85%, 90%, 95% or more of the cells in the composition or of the NK cells in the composition.

Also provided herein are compositions that are suitable for cryopreserving engineered NK cells. In some embodiments, the composition comprises an engineered NK cell and a cryoprotectant. In some embodiments, the cryoprotectant is or comprises DMSO and/or s glycerol. In some embodiments, compositions formulated for cryopreservation can be stored at low temperatures, such as ultra low temperatures, for example, storage with temperature ranges from −40° C. to −150° C., such as or about 80° C.±6.0° C.

In some embodiments, the engineered NK cells can be preserved at ultra low temperature before the administration to a patient. The engineered NK cells can also be preserved at ultra low temperature after isolation from a mammalian subject and prior to the genetic engineering. For example, lymphocytes or another source of engineered NK cells can be isolated, stored at ultra low temperature and then processed to yield engineered NK cells. Alternatively, the lymphocytes or another source of engineered NK cells can be isolated, processed to yield engineered NK cells and then stored at ultra-low temperature.

A typical method for the preservation at ultra low temperature in small scale is described, for example, in U.S. Pat. No. 60,168,991. For small-scale, cells can be preserved at ultra low temperature by low density suspension (e.g., at a concentration of about 200×106/ml) in 5% human albumin serum (HAS) which is previously cooled. An equivalent amount of 20% DMSO can be added into the HAS solution. Aliquots of the mixture can be placed into vials and frozen overnight inside an ultra low temperature chamber at about −80° C.

In some embodiments, the cryopreserved NK cells are prepared for administration by thawing. In some cases, the NK cells can be administered to a subject immediately after thawing. In such an embodiment, the composition is ready-to-use without any further processing. In other cases, the NK cells are further processed after thawing, such as by resuspension with a pharmaceutically acceptable carrier, incubation with an activating or stimulating agent, or are activated washed and resuspended in a pharmaceutically acceptable buffer prior to administration to a subject.

Kits comprising engineered cells are also provided herein. For example, in some embodiment provided herein is a kit comprising an engineered cell and an additional agent. In some embodiments, the additional agent comprises an Fc domain. In some embodiment the additional agent is an Fc fusion protein or an antibody. In some embodiments, the additional agent is a human, humanized, or chimeric antibody. In some of these embodiments, the additional agent is a full length antibody. Exemplary antibodies are described below.

IV. Methods of Treatment

In some embodiments, provided herein is a method of treating a condition in an individual, comprising administering engineered NK cells to an individual in need thereof.

In some embodiments, the method comprises administering an effective amount of engineered cells to an individual. In some embodiments, from or from about $10^5$ to about $10^{12}$ cells, or about $10^5$ to about $10^8$ cells, or about $10^6$ to about $10^{12}$ cells, or about $10^8$ to about $10^{11}$ cells, or about $10^9$ to about $10^{10}$ cells. In some embodiments, the composition comprises, about $10^5$, about $10^6$, about $10^7$, about $10^8$, about $10^9$, about $10^{10}$, about $10^{11}$, or about $10^{12}$ cells are administered to the individual. In some embodiments, from or from about $10^6$ to $10^{10}$ engineered NK cells/kg are administered to the subject.

In some embodiments, the engineered NK cells are administered to an individual soon after isolation and the engineering of the NK cells. In some embodiments, the engineered NK cells are administered to an individual within 1, 2, 3, 4, 5, 6, 7, 14, 21, or 28 days of isolation and the engineering.

In other embodiments, the engineered NK cells are stored or expanded by growth in culture prior to administration and/or engineering, such as by methods described above. For example, the NK cells can be stored for greater than 6, 12, 18, or 24 months prior to engineering and/or administration to the individual.

In some cases, clonal cell lines of NK cells are derived from cancerous cells and thus may divide out of control upon administration to a patient. In some embodiments, the engineered NK cells, such as those from clonal cell lines, may be irradiated prior to administration to a subject to prevent them from dividing out of control.

The engineered NK cells can be can be administered to a subject by any convenient route including parenteral routes such as subcutaneous, intramuscular, intravenous, and/or epidural routes of administration.

The provided engineered NK cells and compositions can be used in methods of treating an individual with a tumor or hyperproliferative disorders or microbial infection such as a viral infection, yeast infection, fungal infection, protozoan infection and/or bacterial infection. The disclosed methods of treating a subject with the engineered cells can be in combination with a therapeutic monoclonal antibody, such as an anti-tumor antigen or anti-cancer antibody, anti-viral antibody or anti-bacterial antibody. The engineered NK cells can be administered for treatment of animals, such as mammalian animals, for example human subjects.

In some examples, the methods include treating a hyperproliferative disorder, such as a hematological malignancy or a solid tumor. Examples of types of cancer and proliferative disorders that can be treated with the compositions described herein include, but are not limited to, leukemia (e.g., myeloblastic, promyelocytic, myelomonocytic, monocytic, erythroleukemia, chronic myelocytic (granulocytic) leukemia, and chronic lymphocytic leukemia), lymphoma (e.g., Hodgkin's disease and non-Hodgkin's disease), fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilm's tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia. The treatment and/or prevention of cancer includes, but is not limited to, alleviating one or more symptoms associated with cancer, the inhibition or reduction of the progression of cancer, the promotion of the regression of cancer, and/or the promotion of the immune response.

In some examples, the methods include treating a viral infection, such as an infection caused by the presence of a virus in the body. Viral infections include chronic or persistent viral infections, which are viral infections that are able to infect a host and reproduce within the cells of a host over a prolonged period of time-usually weeks, months or years, before proving fatal. Viruses giving rise to chronic infections that which may be treated in accordance with the present invention include, for example, the human papilloma viruses (HPV), Herpes simplex, and other herpes viruses, the viruses of hepatitis B and C as well as other hepatitis viruses, human immunodeficiency virus, and the measles virus, all of which can produce important clinical diseases. Prolonged infection may ultimately lead to the induction of disease which may be, e.g., in the case of hepatitis C virus liver cancer, fatal to the patient. Other chronic viral infections which may be treated in accordance with the present invention include Epstein Barr virus (EBV), as well as other viruses such as those which may be associated with tumors.

Examples of viral infections which can be treated or prevented with the compositions and methods described herein include, but are not limited to, viral infections caused by retroviruses (e.g., human T-cell lymphotrophic virus (HTLV) types I and II and human immunodeficiency virus (HIV)), herpes viruses (e.g., herpes simplex virus (HSV) types I and II, Epstein-Ban virus and cytomegalovirus), arenaviruses (e.g., lassa fever virus), paramyxoviruses (e.g., morbillivirus virus, human respiratory syncytial virus, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., Sendai virus and influenza viruses A, B and C), papovaviruses (e.g., papillomaviruses), picornaviruses (e.g., rhinoviruses, enteroviruses and hepatitis A viruses), poxviruses, reoviruses (e.g., rotaviruses), togaviruses (e.g., rubella virus), and rhabdoviruses (e.g., rabies virus). The treatment and/or prevention of a viral infection includes, but is not limited to, alleviating one or more symptoms associated with said infection, the inhibition, reduction or suppression of viral replication, and/or the enhancement of the immune response.

In some embodiments, the compositions are used in a method of treating a yeast or bacterial infection. For example, the compositions and methods described herein can treat infections relating to *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholera, Escherichia coli, Pseudomonas aeruginosa, Campylobacter (Vibrio) fetus, Campylobacterjejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponemapertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella aborts, Brucella suis, Brucella melitensis, Mycoplasma* spp., *Rickettsiaprowazeki, Rickettsia tsutsugumushi, Chlamydia* spp., *Helicobacter pylori* or combinations thereof.

V. Combination Therapy

In some embodiments, the presently engineered NK cells exhibit enhanced activity when activated by antibodies or Fc-containing proteins. For example, the engineered cells can be activated by antibody-mediated crosslinking of CD16 or by antibody-coated tumor cells.

In some embodiments, provided herein is a method of treating a condition in an individual comprising administering an engineered NK cell and an antibody. One of ordinary skill in the art can select an appropriate therapeutic (e.g., anti-cancer) monoclonal antibody to administer to the subject with the engineered NK cells described herein, such as depending on the particular disease or condition of the individual. Suitable antibodies may include polyclonal, monoclonal, fragments (such as Fab fragments), single chain antibodies and other forms of specific binding molecules.

Abs may further comprise humanized or human Abs. Humanized forms of non-human Abs are chimeric Igs, Ig chains or fragments (such as Fv, Fab, Fab', F(ab')2 or other antigen-binding subsequences of Abs) that contain minimal sequence derived from non-human Ig. In some embodiments, the antibody comprises an Fc domain.

Generally, a humanized antibody has one or more amino acid residues introduced from a non-human source. These non-human amino acid residues are often referred to as "import" residues, which are typically taken from an "import" variable domain. Humanization is accomplished by substituting rodent CDRs or CDR sequences for the corresponding sequences of a human antibody (Jones et al., 1986; Riechmann et al., 1988; Verhoeyen et al., 1988). Such "humanized" Abs are chimeric Abs (1989), wherein substantially less than an intact human variable domain has been substituted by the corresponding sequence from a non-human species. In practice, humanized Abs are typically human Abs in which some CDR residues and possibly some Fc residues are substituted by residues from analogous sites in rodent Abs. Humanized Abs include human Igs (recipient antibody) in which residues from a complementary determining region (CDR) of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized Abs may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Jones et al., 1986; Presta, 1992; Riechmann et al., 1988).

Human Abs can also be produced using various techniques, including phage display libraries (Hoogenboom et al., 1991; Marks et al., 1991) and the preparation of human mAbs (Boerner et al., 1991; Reisfeld and Sell, 1985). Similarly, introducing human Ig genes into transgenic animals in which the endogenous Ig genes have been partially or completely inactivated can be exploited to synthesize human Abs. Upon challenge, human antibody production is observed, which closely resembles that seen in humans in all respects, including gene rearrangement, assembly, and antibody repertoire (1997a; 1997b; 1997c; 1997d; 1997; 1997; Fishwild et al., 1996; 1997; 1997; 2001; 1996; 1997; 1997; 1997; Lonberg and Huszar, 1995; Lonberg et al., 1994; Marks et al., 1992; 1997; 1997; 1997).

Specifically, the cells of the present invention can be targeted to tumors by administration with an antibody that recognizes a tumor associated antigen. One of ordinary skill in the art will appreciate that the present engineered NK cells are suitable for use with a wide variety of antibodies that recognize tumor associated antigens. Non-limiting examples of a tumor associated antigen includes CD19, CD20, CD22, CD30, CD33, CD37, CD38, CD40, CD52, CD56, CD70, CD74, CD140, EpCAM, CEA, gpA33, mesothelin, α-fetoprotein, Mucin, PDGFR-alpha, TAG-72, CAIX, PSMA, folate-binding protein, scatter factor receptor kinase, a ganglioside, cytokerain, frizzled receptor, VEGF, VEGFR, Integrin αVβ3, integrin α5β1, EGFR, EGFL7, ERBB2 (HER2), ERBB3, fibronectin, HGF, HER3, LOXL2, MET, IGF1R, IGLF2, EPHA3, FR-alpha, phosphatidylserine, Syndecan 1, SLAMF7 (CD319), TRAILR1, TRAILR2, RANKL, FAP, vimentin or tenascin. In some cases, the antibody is an anti-CD20 antibody, an anti-HER2 antibody, an anti-CD52 antibody, an anti-EGFR antibody and an anti-CD38 antibody. Exemplary antibodies include rituximab, trastuzumab, aletuzumab, certuximab, daratumumab, veltuzumab, ofatumumab, ublituximab, ocaratuzumab. Antibodies specific for a selected cancer type can be chosen, and include any antibody approved for treatment of cancer. Examples include trastuzumab (Herceptin) for breast cancer, rituximab (Rituxan) for lymphoma, and cetuximab (Erbitux) for head and neck squamous cell carcinoma. A skilled artisan is familiar with FDA-approved monoclonal antibodies able to bind particular tumor or disease antigens, any of which can be used in accord with the provided methods for treating the tumor or disease.

The engineered NK cells and the additional agent can be administered sequentially or simultaneously. In some embodiments, the additional agent can be administered before administration of the engineered NK cells. In some embodiments, the additional agent can be administered after administration of the NK cells. For example, the engineered NK cells can be administered simultaneously with antibodies specific for a selected cancer type. Alternatively, the engineered NK cells can be administered at selected times that are distinct from the times when antibodies specific for a selected cancer type are administered.

In particular examples, the subject is administered an effective dose of an antibody before, after, or substantially simultaneously with the population of engineered NK cells. In some examples, the subject is administered about 0.1 mg/kg to about 100 mg/kg of the antibody (such as about 0.5-10 mg/kg, about 1-20 mg/kg, about 10-50 mg/kg, about 20-100 mg/kg, for example, about 0.5 mg/kg, about 1 mg/kg, about 2 mg/kg, about 3 mg/kg, about 4 mg/kg, about 5 mg/kg, about 8 mg/kg, about 10 mg/kg, about 16 mg/kg, about 20 mg/kg, about 24 mg/kg, about 36 mg/kg, about 48 mg/kg, about 60 mg/kg, about 75 mg/kg, or about 100 mg/kg). An effective amount of the antibody can be selected by a skilled clinician, taking into consideration the particular antibody, the particular disease or conditions (e.g. tumor or other disorder), the general condition of the subject, any additional treatments the subject is receiving or has previously received, and other relevant factors. The subject is also administered a population of modified NK cells described herein. Both the antibody and the population of modified NK cells are typically administered parenterally, for example intravenously; however, injection or infusion to a tumor or close to a tumor (local administration) or administration to the peritoneal cavity can also be used. One of skill in the art can determine appropriate routes of administration.

The engineered NK cells can also be administered simultaneously or sequentially with anti-microbial, anti-viral and other therapeutic agents. In some embodiments of the present invention, the engineered cells can be administered to an individual in combination with cytokines and/or growth factors. According to some embodiments of the present invention the at least one growth factor comprises a growth factor selected from the group consisting of SCF, FLT3, IL-2, IL-7, IL-15, IL-12 and IL-21. In some embodiments, the engineered NK cells and the cytokines or growth factors are administered sequentially. For example, the engineered NK cells may be administered first, followed by administration of the cytokines and/or growth factors. In some embodiments, the engineered NK cells are administered simultaneously with the cytokines or growth factors.

In some embodiments, the subject is administered one or more cytokines (such as IL-2, IL-15, IL-21, and/or IL-12) to support survival and/or growth of NK cells. The cytokine(s) can be administered before, after, or substantially simultaneously with the NK cells. In some examples, the cytokine(s) can be administered after the NK cells. In one specific example, the cytokine(s) is administered to the subject within about 1-8 hours (such as within about 1-4 hours, about 2-6 hours, about 4-6 hours, or about 5-8 hours) of the administration of the NK cells.

In some embodiments, the provided methods also can include administering engineered NK cells to an individual in combination with a chemotherapeutic agent. In some embodiments, the chemotherapeutic agent may comprise cyclophosphamide, fludarabine, methyl prednasone In some embodiments, the chemotherapeutic agent is selected from the group consisting of: thalidomide, cisplatin (cis-DDP), oxaliplatin, carboplatin, anthracenediones, mitoxantrone; hydroxyurea, methylhydrazine derivatives, procarbazine (N-methylhydrazine, MM), adrenocortical suppressants, mitotane (.omicron., rho.'-DDD), aminoglutethimide, RXR agonists, bexarotene, tyrosine kinase inhibitors, imatinib, mechlorethamine, cyclophosphamide, ifosfamide, melphalan (L-sarcolysin), chlorambucil, ethylenimines, methylmelamines, hexamethylmelamine, thiotepa, busulfan, carmustine (BCNU), semustine (methyl-CCNTJ), lomustine (CCNU), streptozocin (streptozotocin), DNA synthesis antagonists, estramustine phosphate, triazines, dacarbazine (OTIC, dimethyl-triazenoimidazolecarboxamide), temozolomide, folic acid analogs, methotrexate (amethopterin), pyrimidine analogs, fiuorouracin (5-fluorouracil, 5-FU, 5FTJ), floxuridine (fluorodeox>'uridine, FUdR), cytarabine (cytosine arabinoside), gemcitabine, purine analogs, mercaptopurine (6-mercaptopurine, 6-MP), thioguanine (6-thioguanine, TG), pentostatin (2'-deoxycoformycin, deoxycoformycin), cladribine and fludarabine, topoisomerase inhibitors, amsacrine, vinca alkaloids, vinblastine (VLB), vincristine, taxanes, paclitaxel, protein bound paclitaxel (Abraxane®), docetaxel (Taxotere®); epipodophyllotoxins, etoposide, teniposide, camptothecins, topotecan, irinotecan, dactinomycin (actinomycin D), daunorubicin (daunomycin, rubidomycin), doxorubicin, bleomycin, mitomycin (mitomycin C), idarubicin, epirubicin, buserelin, adrenocorticosteroids, prednisone, progestins, hydroxyprogesterone caproate, medroxyprogesterone acetate, megestrol acetate, diethylstilbestrol, ethinyl estradiol, tamoxifen, anastrozole; testosterone propionate, fluoxymesterone, flutamide, bicalutamide, and leuprolide.

In some embodiments, the cancer drug is thalidomide or its derivatives. In some embodiments, the cancer drug is selected from the group consisting of cisplatin, carboplatin, and oxaliplatin. In certain embodiments, the cancer drug is selected from the group consisting of paclitaxel, Abraxane®, and Taxotere®. In one embodiment, the chemotherueptic agent is selected from the group consisting of asparaginase, bevacizumab, bleomycin, doxorubicin, epirubicin, etoposide, 5-fluorouracil, hydroxyurea, streptozocin, and 6-mercaptopurine, cyclophosphamide, paclitaxel, and gemcitabine.

VI. Exemplary Embodiments

Among the provided embodiments herein are:

1. An engineered natural killer (NK) cell, wherein the NK cell is genetically engineered to reduce FcRγ chain expression, activity and/or signaling in the cell.

2. The engineered NK cell of embodiment 1, wherein the engineered NK cell comprises:
a genetic disruption of a gene encoding FcRγ chain and/or a genetic disruption resulting in reduced expression of FcRγ chain in the engineered NK cell;
a genetic disruption of a gene encoding a protein regulating expression or activity of FcRγ chain and/or a genetic disruption resulting in reduced expression of a protein regulating expression or activity of FcRγ chain; and/or
a genetic disruption of a gene encoding a protein involved in FcRγ chain-dependent signaling and/or a genetic disruption resulting in reduced expression of a protein involved in FcRγ chain-dependent signaling.

3. The engineered NK cell of embodiment 2, wherein the genetic disruption comprises a deletion, mutation and/or insertion resulting in a premature stop codon in the gene or a frameshift of the open reading frame of the gene.

4. The engineered NK cell of embodiment 2 or embodiment 3, wherein both alleles of the gene encoding FcRγ chain, the gene encoding a protein regulating expression or activity of FcRγ chain and/or the gene encoding a protein involved in FcRγ chain-dependent signaling are disrupted in the engineered NK cells.

5. The engineered NK cell of embodiment 1, wherein the engineered NK cell comprises an inhibitory nucleic acid molecule targeting a gene in the NK cell resulting in reduced expression of FcRγ chain, reduced expression of a protein regulating expression or activity of FcRγ chain and/or reduced expression of a protein involved in FcRγ chain-dependent signaling.

6. The engineered NK cell of any of embodiments 2-5, wherein the expression of FcRγ chain, a protein regulating expression or activity of FcRγ chain and/or a protein involved in FcRγ chain-dependent signaling is reduced by greater than or greater than about 50%, 60%, 70%, 80%, 90%, or 95% as compared to the expression of the protein in the NK cell that is not genetically engineered.

7. The engineered NK cell of any of embodiments 2-6, wherein expression of a protein regulating expression or activity of FcRγ chain is reduced in the engineered NK cell and the protein is a transcription factor.

8. The engineered NK cell of embodiment 7, wherein the transcription factor is PLZF (ZBTB16) or HELIOS (IKZF2).

9. The engineered NK cell of any of embodiments 2-6, wherein the expression of a protein involved in FcRγ chain-dependent signaling is reduced in the engineered NK cell and the protein is a downstream signaling molecule.

10. The engineered NK cells of embodiment 9, wherein the downstream signaling molecule is SYK, DAB2 or EAT-2.

11. The engineered NK cell of any of embodiments 2-6, wherein expression of FcRγ chain is reduced in the engineered cell.

12. An engineered NK cell comprising a genetic disruption in a gene encoding FcRγ chain, wherein expression of FcRγ is reduced in the cell.

13. The engineered NK cell of embodiment 12, wherein the genetic disruption comprises a deletion, mutation and/or insertion resulting in a premature stop codon in the gene or a frameshift of the open reading frame of the gene.

14. The engineered NK cell of embodiment 12 or embodiment 13, wherein both alleles of the gene encoding FcRγ chain are disrupted in the genome of the engineered NK cell.

15. The engineered NK cell of any of embodiments 1, 5 or 6, wherein the engineered NK cell comprises an inhibitory nucleic acid molecule that targets a gene encoding FcRγ chain.

16. The engineered NK cell of embodiment 15, wherein the inhibitory nucleic acid molecule comprises a sequence complementary to the gene encoding FcRγ chain.

17. The engineered NK cell of any of embodiments 11-16, wherein the expression of FcRγ chain is reduced by greater 18. The engineered NK cell of any of embodiments 5-6 and 15-17, wherein the inhibitory nucleic acid comprises an RNA interfering agent.

19. The engineered NK cell of any of embodiments 5-6 and 15-18, wherein the inhibitory nucleic acid comprises siRNA, shRNA, or miRNA.

20. The engineered NK cell of any of embodiments 1-19, wherein the reduced expression, activity and/or signaling of FcRγ is permanent, transient or inducible.

21. The engineered NK cell of any of embodiments 1-20, wherein the expression, activity and/or signaling of FcRγ chain is reduced by greater than or greater than about 50%, 60%, 70%, 80%, 90%, or 95% as compared to the expression, activity and/or signaling in the NK cell that is not genetically engineered.

22. The engineered NK cell of any one of embodiments 1-21, wherein the expression of FcRγ chain expressed in the cell is undetectable in an immunoblot assay.

23. The engineered NK cell of any of embodiments 1-22, wherein CD16 is expressed on the surface of the engineered NK cell.

24. The engineered NK cell of any one of embodiments 1-23, wherein the engineered NK cell expresses CD3-zeta (CD3ζ) chain.

25. The engineered NK cell of any one of embodiments 1-24 that is derived from a primary cell obtained from a subject.

26. The engineered NK cell of embodiment 25, wherein the subject is human.

27. The engineered NK cell of any one of embodiments 1-24 that is derived from a clonal cell line.

28. The engineered NK cell of embodiment 27, wherein the clonal cell line is NK-92, NK-YS, KHYG-1, NKL, NKG, SNK-6, or IMC-1.

29. The engineered NK cell of any of embodiments 1-28, wherein the engineered NK cell comprises a recombinant or heterologous CD16 gene and/or a recombinant or heterologous CD3-zeta (CD3ζ) chain.

30. The engineered NK cell of embodiment 29, wherein the CD16 comprises a CD16-activating mutation, a mutation that results in higher affinity to IgG1, a 158V mutation and/or a 158F mutation.

31. The engineered cell of any of embodiments 1-30, wherein the engineered NK cell exhibits increased activity when stimulated through CD16 compared to the NK cell without the modification.

32. The engineered NK cell of any one of embodiments 1-31, wherein the engineered NK cell has reduced surface expression of NKp46, NKp30, and/or NKp44 compared to the NK cell without the modification.

33. A method of producing an engineered NK cell, comprising genetically engineering an NK cell to reduce FcRγ chain expression, activity, and/or signaling in the cell.

34. The method of embodiment 33, wherein reducing expression comprises:
   disrupting or repressing a gene encoding FcRγ chain and/or disrupting or repressing a gene that results in reduced expression of FcRγ chain in the NK cell;
   disrupting or repressing a gene encoding a protein regulating expression or activity of FcRγ chain and/or a disrupting or repressing a gene that results in reduced expression of a protein regulating expression or activity of FcRγ chain in the NK cell; and/or
   disrupting or repressing a gene encoding a protein involved in FcRγ chain-dependent signaling and/or a disrupting or repressing a gene that results in reduced expression of a protein involved in FcRγ chain-dependent signaling in the NK cell.

35. The method of embodiment 33 or embodiment 34, comprising introducing a deletion, mutation, or insertion into the gene.

36. The method of any one of embodiments 33-35, wherein the gene encodes FcRγ chain.

37. The method of any one of embodiments 33-35 wherein the gene encodes a protein regulating expression or activity of FcRγ chain that is a transcription factor.

38. The method of embodiment 37, wherein the transcription factor is PLZF or HELIOS.

39. The method of any one of embodiments 33-35, wherein the gene encodes a protein involved in FcRγ chain-dependent signaling that is a downstream signaling molecule.

40. The method of embodiment 38, wherein the downstream signaling molecule is SYK, DAB2 or EAT2.

41. The method of any of embodiments 33-40, wherein disruption or repression of the gene is effected by introducing an endonuclease that target to the gene in the NK cell under conditions that allow disruption or repression of the gene.

42. The method of embodiment 41, wherein the endonuclease is selected from the group consisting of TAL nucleases, meganucleases, zinc-finger nucleases, Cas9, and Argonaute.

43. The method of any of embodiments 33-40, wherein disruption or repression is effected by introducing an inhibitory nucleic acid that targets the gene into the NK cell under conditions that results in repression of the gene.

44. The method of embodiment 43, wherein the inhibitory nucleic acid molecule comprises a sequence complementary to the gene encoding FcRγ chain.

45. The method of embodiment 43 or embodiment 44, wherein the inhibitory nucleic acid comprises an RNA interfering agent.

46. The method of any one of embodiments 43-45, wherein the nucleic acid is siRNA, shRNA, or miRNA.

47. The method of any one of embodiments 33-46, wherein the reduced expression is permanent, transient, or inducible.

48. The method of any one of embodiments 33-47, wherein the expression, activity and/or signaling of FcRγ chain is reduced by greater than or greater than about 50%, 60%, 70%, 80%, 90%, or 95% as compared to the expression in the NK cell in that is not genetically engineered.

49. The method of any one of embodiments 33-48, wherein the FcRγ chain expression level is not detectable by an immunoblot assay.

50. The method of any one of embodiments 33-49, comprising, prior to the genetically engineering, isolating the NK cell from a human subject.

51. The method of embodiment 50, comprising isolating the NK cell from peripheral blood mononuclear cells (PBMC).

52. The method of embodiment 50 or 51, wherein isolating the NK cell comprises selecting NK cells from PBMC using a NK cell marker.

53. The method of embodiment 52, wherein the NK cell marker is CD56, Cd161, KIR, NKG2A, NKG2D, NKp30, NKp44, and/or NKp46.

54. The method of any one of embodiments 50-53, further comprising selecting NK cells that express CD16 and/or CD3ζ.

55. The method of any one of embodiments 50-54, further comprising selecting NK cells that do not express surface CD3.

56. The method of any one of embodiments 33-49, wherein the NK cell is an NK cell line.

57. The method of embodiment 56, wherein the cell line is NK-92, NK-YS, KHYG-1, NKL, NKG, SNK-6, or IMC-1.

58. The method of embodiment 56 or embodiment 57, further comprising engineering the NK cell line to express a recombinant or heterologous CD16 and/or CD3ζ.

59. The method of embodiment 58, comprising introducing nucleic acid encoding the CD16 and/or CD3ζ into the NK cell.

60. The method of embodiment 58 or embodiment 59, wherein the CD16 gene contains an activating mutation and/or a mutation that increases affinity of CD16 for IgG.

61. The method of any of embodiments 58-60, wherein the CD16 comprises a mutation that is 158V.

62. The method of any of embodiments 58-60, wherein the CD16 comprises a mutation that is 158F.

63. The method of any of embodiments 58-62, comprising virally transducing the NK cell with nucleic acid encoding the CD16 and/or CD3ζ.

64. The method of any of embodiments 58-62, comprising transfecting the NK cell with nucleic acid encoding the CD16 and/or CD3ζ.

65. The method of any one of embodiments 58-64, comprising transiently, inducibly, or permanently expressing CD16 or CD3ζ in the NK cell.

66. The method of any one of embodiments 33-65, further comprising culturing or expanding the engineered NK cells.

67. The method of embodiment 66, comprising culturing the engineered NK cells with feeder cells.

68. The method of embodiment 66 or embodiment 67 comprising culturing the engineered NK cells with cytokines.

69. An engineered NK cell produced by the methods of any one of embodiments 33-68.

70. A composition comprising an effective amount of the engineered NK cell of any one of embodiments 1-32, or 69.

71. The composition of embodiment 70, further comprising a pharmaceutically acceptable carrier.

72. The composition of embodiment 71, wherein the carrier is a saline solution, a dextrose solution, or 5% human serum albumin.

73. The composition of any one of embodiments 70-72, wherein the composition comprises between $1 \times 10^5$ and $1 \times 10^8$ cells/mL.

74. The composition of any of embodiments 70-73 comprising a cryoprotectant.

75. A kit comprising the engineered cell of any one of embodiments 1-32, or 69 or a composition of any one of embodiments 70-74 and an additional agent for treatment of a disease.

76. The kit of embodiment 75, wherein the additional agent is an antibody or an Fc-fusion protein.

77. The kit of embodiment 76, wherein the antibody recognizes or specifically binds a tumor associated antigen.

78. The kit of embodiment 77, wherein the tumor associated antigen is CD19, CD20, CD22, CD30, CD33, CD37, CD38, CD40, CD52, CD56, CD70, CD74, CD140, EpCAM, CEA, gpA33, mesothelin, α-fetoprotein, Mucin, PDGFR-alpha, TAG-72, CAIX, PSMA, folate-binding protein, scatter factor receptor kinase, a ganglioside, cytokerain, frizzled receptor, VEGF, VEGFR, Integrin αVβ3, integrin α5β1, EGFR, EGFL7, ERBB2 (HER2), ERBB3, fibronectin, HGF, HER3, LOXL2, MET, IGF1R, IGLF2, EPHA3, FR-alpha, phosphatidylserine, Syndecan 1, SLAMF7 (CD319), TRAILR1, TRAILR2, RANKL, FAP, vimentin or tenascin.

79. The kit of any one of embodiments 76-78, wherein the antibody is a full length antibody and/or comprises an Fc domain.

80. A method of treating a condition comprising administering engineered NK cells of any one of embodiments 1-32, or 69 or a composition of any one of embodiments 70-74 to an individual in need thereof.

81. The method of embodiment 80, wherein prior to administering the engineered NK cells producing the engineered NK cells by the method of any of embodiments 33-68.

82. The method of embodiment 80 or embodiment 81, comprising administering from or from about $1 \times 10^8$ to $1 \times 10^{10}$ cells/m$^2$ to the individual or administering from or from about $1 \times 10^6$ to $1 \times 10^{10}$ NK cells/kg.

83. The method of any one of embodiments 80-82 further comprising administering an additional agent.

84. The method of embodiment 83, wherein the additional agent is an antibody or an Fc-fusion protein.

85. The method of embodiment 84 wherein the antibody recognizes a tumor associated antigen.

86. The method of embodiment 84 or embodiment 85, wherein the tumor associated antigen is CD19, CD20, CD22, CD30, CD33, CD37, CD38, CD40, CD52, CD56, CD70, CD74, CD140, EpCAM, CEA, gpA33, mesothelin, α-fetoprotein, Mucin, PDGFR-alpha, TAG-72, CAIX, PSMA, folate-binding protein, scatter factor receptor kinase, a ganglioside, cytokerain, frizzled receptor, VEGF, VEGFR, Integrin αVβ3, integrin α5β1, EGFR, EGFL7, ERBB2 (HER2), ERBB3, fibronectin, HGF, HER3, LOXL2, MET, IGF1R, IGLF2, EPHA3, FR-alpha, phosphatidylserine, Syndecan 1, SLAMF7 (CD319), TRAILR1, TRAILR2, RANKL, FAP, vimentin or tenascin.

87. The method of any one of embodiments 84-86, wherein the antibody comprises an Fc domain and/or is a full-length antibody.

88. The method of any one of embodiments 83-87, wherein the additional agent and the engineered NK cells are administered sequentially.

89. The method of embodiment 88, wherein the additional agent is administered prior to administration of the engineered NK cells.

90. The method of any one of embodiments 83-87, where the additional agent and the engineered NK cells are administered simultaneously 91. The method of any one of embodiments 80-90, wherein the condition is selected from the group consisting of an inflammatory condition, an infection, and cancer.

92. The method of embodiment 91, wherein the infection is a viral infection or a bacterial infection.

93. The method of embodiment 92, wherein the cancer is leukemia or lymphoma.

94. The method of embodiment 92, wherein the cancer comprises a solid tumor.

95. The method of any one of embodiments 80-94, wherein the individual is a human.

96. The method of any one of embodiments 80-95, wherein the engineered NK cell is allogenic to the individual.

97. The method of any one of embodiments 80-95, wherein the engineered NK cell is autologous to the subject.

98. The engineered NK cell of any one of embodiments 1-32, wherein the cell is genetically engineered to reduce expression of a NK inhibitory receptor.

99. The engineered NK cell of embodiment 98, wherein:

the cell comprises a genetic disruption of a gene encoding a NK inhibitory receptor and/or a genetic disruption resulting in reduced expression of an NK inhibitory receptor; or the cell comprises an inhibitory nucleic acid that targets a gene encoding a NK inhibitory receptor and/or that reduces expression of an NK inhibitory receptor.

100. The engineered NK cell of embodiment 98 or embodiment 99, wherein the inhibitory receptor is NKG2A or KIR2DL1.

101. The method of any one of embodiments 32-68, further comprising genetically engineering the NK cell to reduce expression or activity of an inhibitory receptor.

102. The method of embodiment 101, wherein reducing expression or activity comprises disrupting or repressing expression of a gene encoding the NK inhibitory receptor or a gene that results in reduced expression of the NK inhibitory receptor.

103. The method of embodiment 102, wherein the inhibitory receptor is NKG2A or KIR2DL1.

VII. Examples

The following examples are included for illustrative purposes only and are not intended to limit the scope of the invention.

Example 1: Assessment of Cell Killing of Expanded G-NK Cells and Conventional NK Cells $25 \times 10^6$ peripheral blood mononuclear cells (PBMCs) from a healthy human donor were obtained, and fluorescence-activated cell sorting was used to enrich $\sim 2 \times 10^5$ FcRγ-deficient (g⁻ NK) cells based on certain cell surface phenotypes. G-NK cells were expanded 250-fold in 14 days by mixing 0.5 mL ($1 \times 10^6$) of feeder cells (irradiated autologous PBMC stimulated with 10 ng/mL OKT3) with 0.5 mL ($2 \times 10^5$) of sorted g-NK cells. The expansion was spiked with 10 ng/mL IL-2 every 2 days and on day 7, expanding g-NK cells were re-fed the cells with irradiated feeders (pre-activated with 10 ng/mL OKT3) at a 5:1 feeder:g-NK cell ratio. Conventional NK cells also were obtained and expanded.

To assess antibody-directed activity of expanded g-NK cells, serial dilutions of the enriched g-NK cells (E/T ratio ranging from 50:1 to 1:1) were incubated in a 96-well plate with $^{51}$Cr-labeled Raji lymphoma cells in the presence or absence of anti-CD20 antibody rituximab (5 μg/mL). After incubation for 4 hours, antibody dependent cell cytotoxicity (ADCC) was assessed by determining $^{51}$Cr activity per well. As shown in FIG. 1, the results showed that g-NK cells exhibited greater ability to mediate ADCC when co-cultured with rituximab and Raji lymphoma cells than conventional NK cells.

The present invention is not intended to be limited in scope to the particular disclosed embodiments, which are provided, for example, to illustrate various aspects of the invention. Various modifications to the engineered cells, compositions and methods described will become apparent from the description and teachings herein. Such variations may be practiced without departing from the true scope and spirit of the disclosure and are intended to fall within the scope of the present disclosure.

What is claimed is:

1. An engineered NK cell that is derived from a primary cell obtained from a human subject or is derived from a clonal cell line, in which a gene encoding FcRγ chain is genetically disrupted to knockout FcRγ in the engineered cell, wherein the genetic disruption of the gene encoding FcRγ increases antibody dependent cellular cytotoxicity (ADCC) via CD16 expressed on the surface of the engineered cell compared to a NK cell that is not genetically engineered with the genetic disruption.

2. The engineered NK cell of claim 1, wherein the expression of FcRγ chain is reduced by greater than or greater than about 50% as compared to the expression of the protein in the NK cell that is not genetically engineered with the genetic disruption.

3. The engineered NK cell of claim 1, wherein the expression of FcRγ chain expressed in the cell is undetectable in an immunoblot assay.

4. The engineered NK cell of claim 1, that is derived from a primary cell obtained from a human subject.

5. The engineered NK cell of claim 1, wherein the CD16 is a heterologous CD16 that comprises a CD16-activating mutation.

6. A method of producing an engineered NK cell, that is derived from a primary cell obtained from a human subject or is derived from a clonal cell line, in which a gene encoding FcRγ chain is genetically disrupted to knockout FcRγ in the engineered cell, wherein the genetic disruption of the gene encoding FcRγ increases antibody dependent cellular toxicity (ADCC) via CD16 expressed on the surface of the engineered cell compared to a NK cell that is not genetically engineered with the genetic disruption.

7. A composition comprising an effective amount of the engineered NK cell of claim 1.

8. A kit comprising the engineered cell of claim 1 and an additional agent for treatment of a disease, wherein the additional agent is an antibody or an Fc-fusion protein.

9. The engineered NK cell of claim 1, wherein the CD16 is a heterologous CD16 that comprises a mutation that results in a higher affinity of CD16 to IgG1.

10. The engineered NK cell of claim 1, wherein the CD16 is a heterologous CD16 that comprises a 158V mutation.

11. The method of claim 6, wherein the NK cell is derived from a primary cell obtained from a human subject.

12. The method of claim 6, wherein the method results in reduced expression of FcRγ chain that is reduced by greater than or greater than about 50% as compared to the expression in the NK cell in that is not genetically engineered.

13. The method of claim 6, wherein the method results in FcRγ chain expression level that is not detectable by an immunoblot assay.

14. The method of claim 6, wherein the genetic disruption is by an endonuclease.

15. The method of claim 14, wherein the endonuclease is a TAL nucleases, meganucleases, zinc-finger nucleases, an Argonaute nuclease or a CRISPR enzyme in combination with a guide RNA.

16. The method of claim 6, wherein the CD16 is a heterologous CD16 and the method comprises introducing a nucleic acid encoding the heterologous CD16 into the NK cell.

17. The method of claim 16, wherein the heterologous CD16 comprises a mutation that results in a higher affinity of CD16 to IgG1.

18. The method of claim 17, wherein the heterologous CD16 comprises a 158V mutation.

\* \* \* \* \*

UNITED STATES PATENT AND TRADEMARK OFFICE
CERTIFICATE OF CORRECTION

PATENT NO. : 11,920,156 B2
APPLICATION NO. : 16/484813
DATED : March 5, 2024
INVENTOR(S) : Guy Dipierro It is certified that error appears in the above-identified patent and that said Letters Patent is hereby corrected as shown below:

In the Claims

At Column 50, Claim number 6, Line 67, please replace "toxicity" with -- cytotoxicity --.

Signed and Sealed this
Twenty-fourth Day of September, 2024

*Katherine Kelly Vidal*

Katherine Kelly Vidal
*Director of the United States Patent and Trademark Office*